(12) United States Patent
Tan et al.

(10) Patent No.: US 9,896,545 B2
(45) Date of Patent: Feb. 20, 2018

(54) BIS(AZOBENZENE) DIAMINES AND PHOTOMECHANICAL POLYMERS MADE THEREFROM

(71) Applicant: The United States of America, as represented by the Secretary of the Air Force, Washington, DC (US)

(72) Inventors: Loon-Seng Tan, Centerville, OH (US); David Huabin Wang, Beavercreek, OH (US); Jeong Jae Wie, Gyeonggi (KR); Timothy J. White, Centerville, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 15/584,464

(22) Filed: May 2, 2017

(65) Prior Publication Data

US 2017/0233529 A1     Aug. 17, 2017

Related U.S. Application Data

(62) Division of application No. 14/845,450, filed on Sep. 4, 2015, now Pat. No. 9,644,071.

(60) Provisional application No. 62/046,433, filed on Sep. 5, 2014, provisional application No. 62/046,372, filed on Sep. 5, 2014.

(51) Int. Cl.
  *C08G 73/10*  (2006.01)
  *C08G 69/32*  (2006.01)
  *C07C 245/08* (2006.01)

(52) U.S. Cl.
  CPC .......... *C08G 73/1007* (2013.01); *C08G 69/32* (2013.01); *C08G 73/10* (2013.01); *C08G 73/1039* (2013.01); *C08G 73/1042* (2013.01); *C08G 73/1067* (2013.01); *C08G 73/1096* (2013.01); *C07C 245/08* (2013.01)

(58) Field of Classification Search
  CPC .... C08G 73/1067; C08G 69/32; C07C 245/08
  See application file for complete search history.

(56) References Cited

PUBLICATIONS

Ravi Shankar et al "Contactless, photoinitiated snap-through in azobenzene-functionalized polymers", Proceedings of the National Academy of Sciences of the United States of America (2013), 110(47), 18792-18797., Nov. 19, 2013.*
USPTO structure search, dated Nov. 2017.*

* cited by examiner

*Primary Examiner* — Gregory Listvoyb
(74) *Attorney, Agent, or Firm* — Afmclo/Jaz; Chastity Whitaker

(57) ABSTRACT

Bis(azo-benzene) diamine monomers and a method of synthesizing the monomers are provided. The bis(azo-benzene) diamine monomers, in combination with amine reactive monomers, form polymers, such as polyimides and copolyimides, having photomechanical and thermomechanical properties.

8 Claims, 12 Drawing Sheets

4a

4b

10a

10b

10c

10d

BIS(AZOBENZENE) DIAMINES AND PHOTOMECHANICAL POLYMERS MADE THEREFROM

This application is a divisional of U.S. application Ser. No. 14/845,450 (pending), filed Sep. 4, 2015, which claims benefit of and priority to U.S. Provisional Patent Application Ser. Nos. 62/046,433 and 62/046,372, each of which was filed on Sep. 5, 2014. The disclosure of each of these applications is incorporated herein by reference, in its entirety.

RIGHTS OF THE GOVERNMENT

The invention described herein may be manufactured and used by or for the Government of the United States for all governmental purposes without the payment of any royalty.

FIELD OF THE INVENTION

The invention generally relates to bis(azobenzene)-containing diamines, as well as the polymers and copolymers made therefrom. More particularly, the invention relates to bis(azobenzene)-containing diamines, which are useful for preparing polyimide, polyamide, and poly(amide-imide) polymers and copolymers having photomechanical properties and methods of making the same.

BACKGROUND

Photomechanical polymers are a special class of stimuli-responsive materials that can transduce light into mechanical work. Photo-initiated shape adaptivity or force generation (actuation) are particularly intriguing due to the salient features of light, namely, remote and wireless (contactless) triggering with ease of spatial, temporal, directional (through polarization), and magnitude (with intensity) control.

Considerable effort has been undertaken in both the synthesis of photoresponsive polymers and the characterization of their photomechanical outputs. To date, azobenzene has been the most-utilized photochromic unit in the examination of amorphous, crystalline, and liquid crystalline polymers because of its excellent thermal stability, resolved isomeric forms, unique optical nonlinearities, and ability to form surface reliefs when subjected to conventional or polarization holography. The resulting photomechanical output of a polymeric material is dependent not only on its optical properties (absorption wavelength, wavelength of exposure, polarization of exposure) but also on its morphology (amorphous, crystalline, liquid crystalline) and thermomechanical properties.

A number of reports have distinguished the photo-responses of liquid crystalline polymer networks (LCN, both glasses and elastomers) for comparatively large magnitude responses typified by bending of cantilevers or dramatic uniaxial contractions of thin films. Notably, a majority of these efforts have characterized the response of azobenzene-based LCN to exposure to UV light, which is known to decrease the order of the LCN through trans-cis photoisomerization and can result in an isothermal phase transition. UV-induced responses in azobenzene LCN are limited in the need for multiple light sources to reverse the trans-cis isomerization.

Comparatively, we have explored the use of 442 nm (or 488 nm) exposure of azobenzene LCN materials and demonstrated distinct photomechanical responses such as polarization controlled forward and reverse bending of a cantilever, as reported in U.S. patent application Ser. No. 13/272,775 filed on Oct. 13, 2011, which is incorporated by reference herein in its entirety. Recently, the photomechanical and thermomechanical response of a glassy polydomain azobenzene LCN has been documented, revealing the close relationship between these two properties.

Heat-resistant polymers such as polyimides (PIs), poly (amide-imides) and polyamides are useful in a variety of applications. Particularly, the wide application of PIs is a result of their excellent combination of physical properties, thermal stability, and processability. For example, PIs containing azobenzene in the backbone or side-chain have been investigated for photo-induced alignment in liquid crystal display (LCD) as well as nonlinear optical applications. More recently, an azobenzene-containing poly(amic acid) (a PI precursor) was crosslinked by a triamine in N,N-dimethylformamide (DMF) and the resulting sol-gels showed a two-fold increase in the storage modulus after irradiation with 405 nm light. And we recently developed a new photomechanical polymer system derived from a multi (azobenzene-amine) cross-linker, an aromatic amine and a dianhydride, as disclosed in U.S. Pat. No. 8,785,589 and U.S. patent application Publication Ser. No. 13/866,524, each of which is incorporated herein by reference in its entirety. The resultant crosslinked azobenzene-containing glassy polyimides possessed favorable photomechanical and thermomechanical responses.

Accordingly, there is a need for new azobenzene-containing monomers, as well as new polymers made therefrom, for new materials having photomechanical and thermomechanical responses.

SUMMARY

In accordance with embodiments of the present invention, a bis(azobenzene)-diamino monomer is provided, which is defined by a general chemical formula (I):

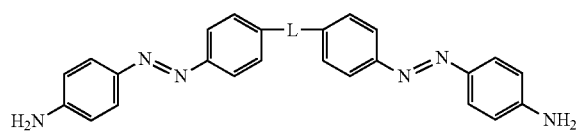

wherein L' is selected from the group consisting of

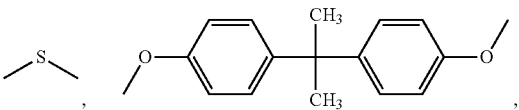

-continued

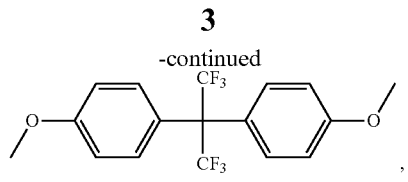

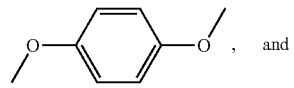, and

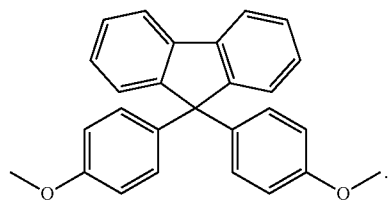

In accordance with another embodiment of the present invention, a bis(azobenzene)-containing polyimide is provided, which is defined by a general chemical formula (II):

-continued

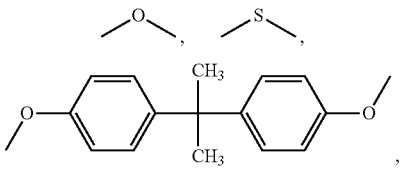, and

;

and
wherein -L- is selected from the group consisting of

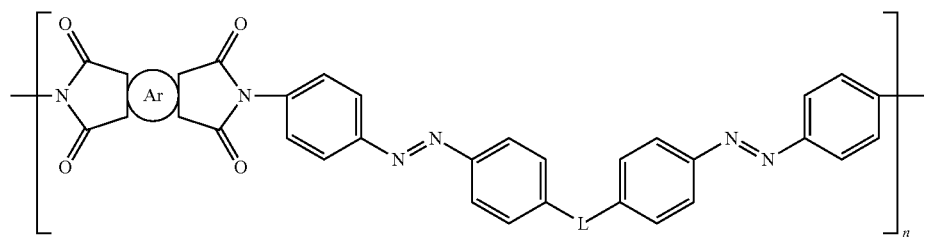

wherein n is a degree of polymerization;
wherein

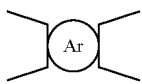

is selected from the group consisting of

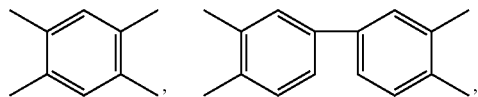,

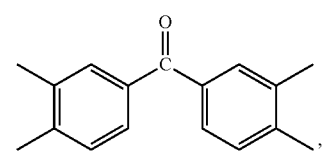,

-continued

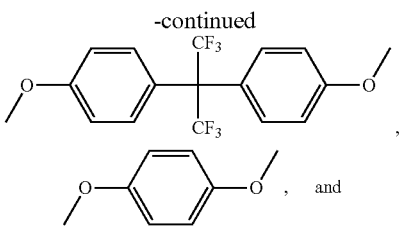,

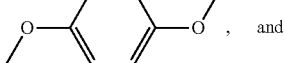, and

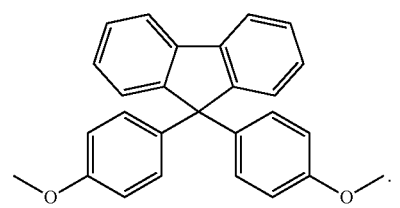.

In accordance with yet another embodiment of the present invention, a bis(azobenzene)-containing copolyimide is provided, which is defined by a general chemical formula (III):

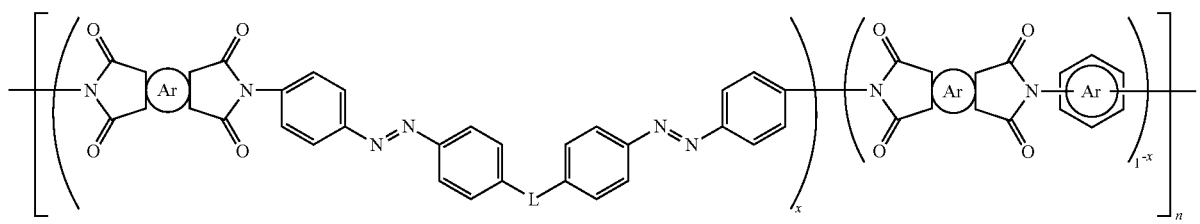

where n is a degree of polymerization; where x is in a range from about 0.01 to about 0.99;
wherein

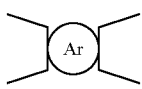

is selected from the group consisting of

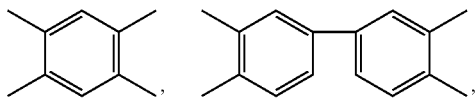

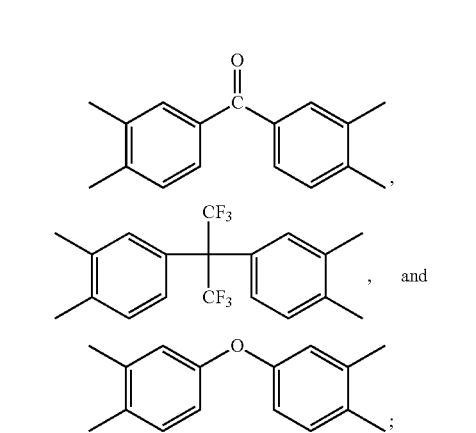

wherein -L- is selected from the group consisting of

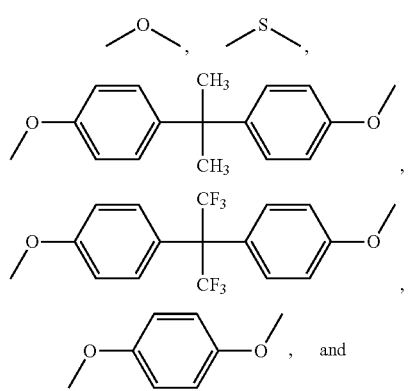

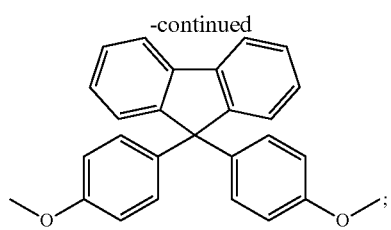

and
wherein

is selected from the group consisting of

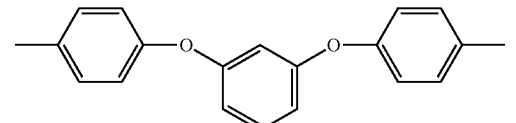

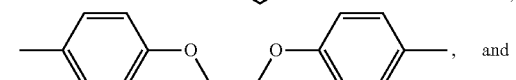

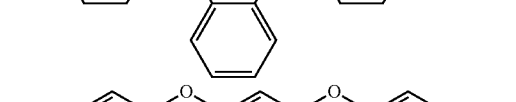

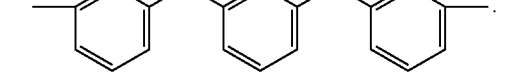

Additional objects, advantages, and novel features of the invention will be set forth in part in the description and drawings which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the invention and, together with the summary given above, and the detailed description given below, serve to explain the invention.

DETAILED DESCRIPTION OF EMBODIMENTS OF THE INVENTION

Embodiments of the present invention overcome an existing need in the prior art by providing new photochromic bis(azobenzene)-diamino monomers, which may be used in the preparation of new linear and crosslinked polyimides, polyamides, or poly(amide-imide)s having photomechanical properties. Representative polyimides and copolyimides, which are derived from the photochromic bis(azobenzene)-diamino monomers are heat resistant and possess excellent photomechanical properties, are further described. As evidence of the photomechanical properties, cantilevers of the linear polyimides show large-amplitude, photo-directed, bidirectional bending. The high modulus and glassy nature of these materials distinguish them for highly efficient and useful light-to-work transduction.

In order to impart high-temperature capability as well as solubility and processability to the resulting photomechanical polyimides, and polyamides and poly(amide-imide)s, the design strategy of the diamine monomer calls for the incorporation of thermally stable yet flexible linkage together with two azobenzene moieties into the molecular structure. In view thereof, herein a bis(azobenzene)-diamino monomer is provided that is defined by the general chemical formula (I):

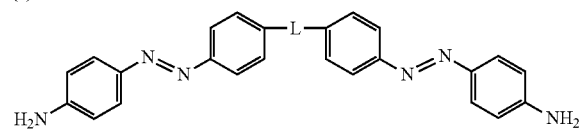

wherein L' is selected from the group consisting of

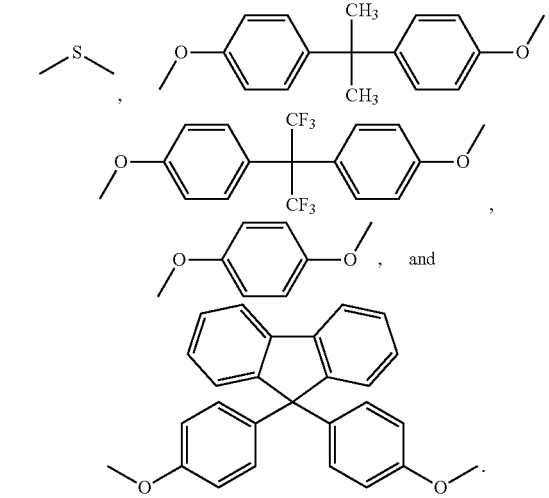

Figure 1:
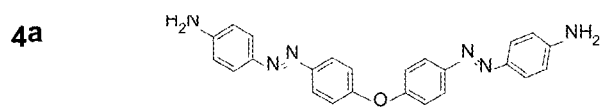
FIG. 1 illustrates molecular structures of representative bis(azobenezene)-diamino monomers.
Figure 1:
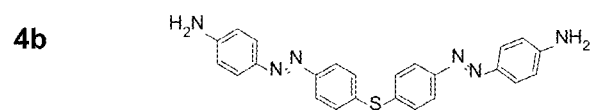
Figure 1:
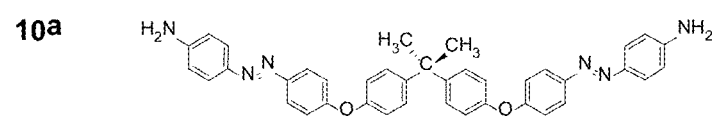
Figure 1:
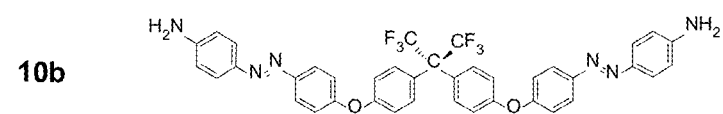
Figure 1:
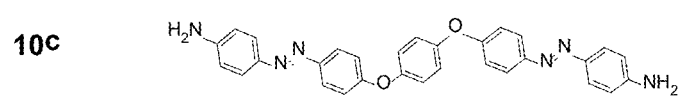
Figure 1:
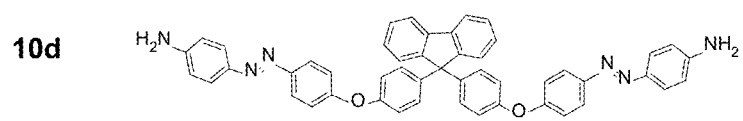

Exemplary bis(azobenzene)-diamino monomers (4b and 10a-10d) are depicted in FIG. 1. Previously-known bis(azobenzene) diamine compound 4a, which was reportedly used in making coordination polymers having antibacterial and antifungal activity (Yogesh et al., Chemical Science Transactions (2013), 2(1), 301-307), was also found to be a suitable bis(azobenzene)-diamino monomer for making photomechanical polymers, as further described below.

Figure 2:
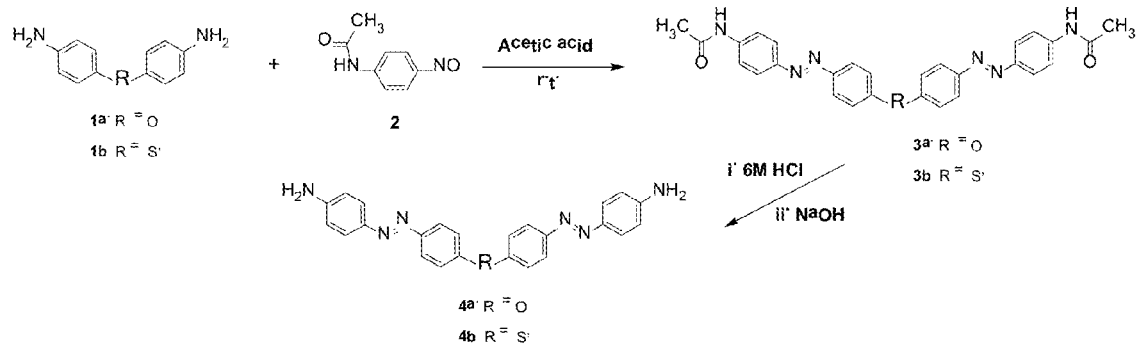
FIG. 2 illustrates exemplary synthetic schemes toward producing bis(azobenezene)-diamino monomers, in accordance with an embodiment of the present invention.
Figure 2:
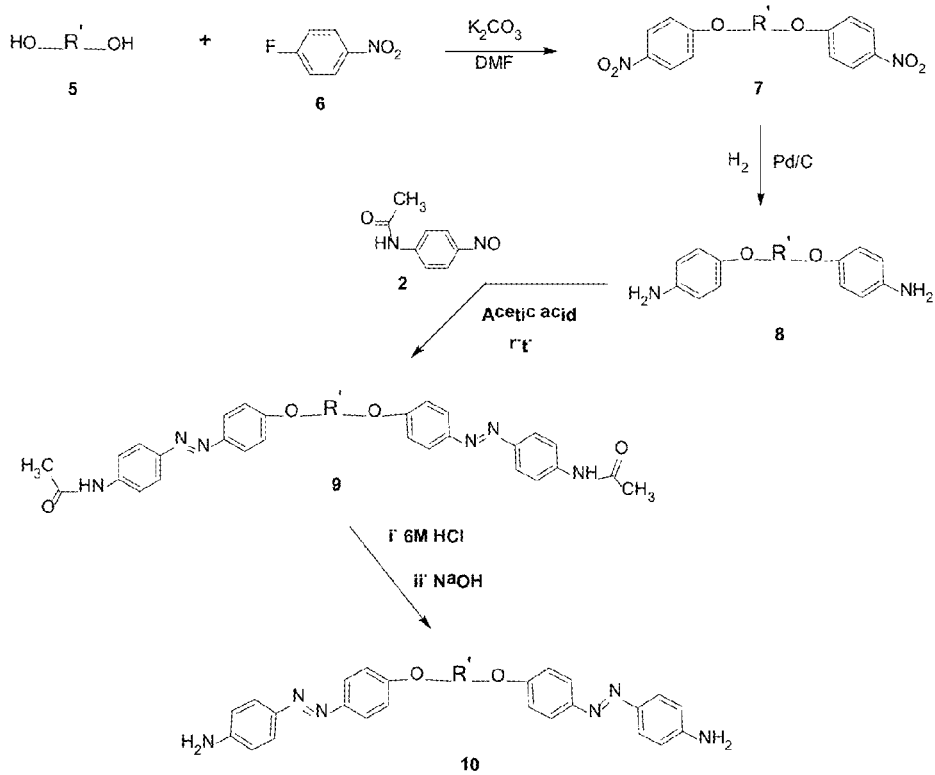
Figure 2:
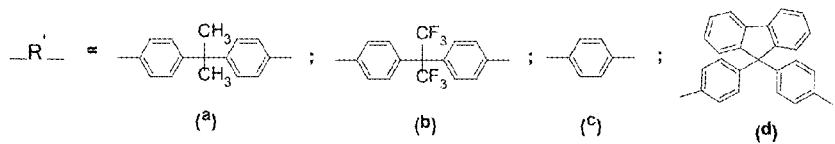

In accordance with another embodiment of the present invention and with reference to FIG. 2, a method for making the bis(azobenzene)-diamino monomers is provided. A double condensation reaction of 4-nitrosoacetanilide (2) and a diamine compound is a key step in the synthesis of the bis(azobenzene) diamines. For readily available relatively flexible diamines (1) such as 4,4'-oxydianiline (1a) and 4,4'-diaminodiphenylsulfide (1b), the synthesis of bis(azobenzene) diamines such as 4a and 4b can be accomplished in two steps, namely bis(azobenzene) formation followed by hydrolysis of the acetyl protecting group to release the diamine, as depicted in Method A of FIG. 2. For less readily available diamines, additional steps are required to prepare the diamine first, as illustrated by Method B of FIG. 2 for the diamine monomers 10a-10d. Treating the appropriate diphenol (5a-d) with 1-fluoro-4-nitrobenzene (6) in the presence of potassium carbonate would provide the corresponding bis-nitrophenyl compounds (7a-d). Reduction of the nitro functional groups would provide the bis-amino compounds (8a-d), which can be coupled with 4-nitrosoacetanilide (2) via a condensation reaction in acetic acid to provide the bis-acetyl protected diamine compounds 9(a-d). Hydrolysis of the acetyl protecting group affords the desired bis(azobenzene) diamine monomers (10a-d).

For example, for the synthesis of 2,2-bis{4-[4-(4-aminophenyldiazenyl) phenoxy]-phenyl}propane (10a) can be realized by treated with 1-fluoro-4-nitrobenzene (6) with 2,2-bis(4-hydroxyphenyl)propane (5a) in the presence of potassium carbonate to yield 2,2-bis[4-(4-nitrophenoxy) phenyl]propane (7a), which was reduced to 2,2-bis[4-(4-aminophenoxy)phenyl]propane (8a) by catalytic hydrogenation. The condensation reaction of (8a) and 4-nitrosoacetanilide (2) in acetic acid yielded the bis-acetylated bis(azobenzene) diamine (9a). The bis(azobenzene)-diamino monomer (10a) was generated after the deprotection of (9a) via de-acetylation reaction in 6M HCl(aq.) solution.

Polymers

It should be appreciated that the foregoing bis(azobenzene)-diamino monomers (4a, 4b, and 10a-d) may be reacted with a variety of amine-reactive monomers to form many types of polymers, copolymers, etc. Non-limiting examples of polymers that may be formed with the bis(azobenzene) diamine monomers (4a, 4b, and 10a-d) include polyimides, polyamides, poly(amide-imide)s, copolyimides, copolyamides, copoly(amide-imide)s, etc.

For example, a typical approach for synthesizing a bis (azobenzene)-containing polyimides includes polymerizing at least one bis(azobenzene)-diamino monomer (such as 4a, 4b, or 10a-d) and a dianhydride monomer in about a stoichiometric ratio (i.e., about a 1:1 molar ratio) to generate a bis(azobenzene)-containing poly(amic acid) precursor, which is then converted to the corresponding bis(azobenzene)-containing polyimide typically by either thermal cure (e.g., by heating to >200° C. in solution or solid state) or chemical imidization using a dehydrating agent or promoter such as acetic anhydride/triethylamine or acetic anhydride/ pyridine. A typical heating schedule includes sequentially heating the bis(azobenzene)-containing poly(amic acid) precursor at about 100° C. for about an hour, at about 150° C. for about an hour, at about 175° C. for about an hour, at about 200° C. for about an hour, at about 250° C. for about an hour, and at about 300° C. for about an hour, to form the imidized bis(azobenzene)-containing polyimides in the form of thin films.

Figure 3:
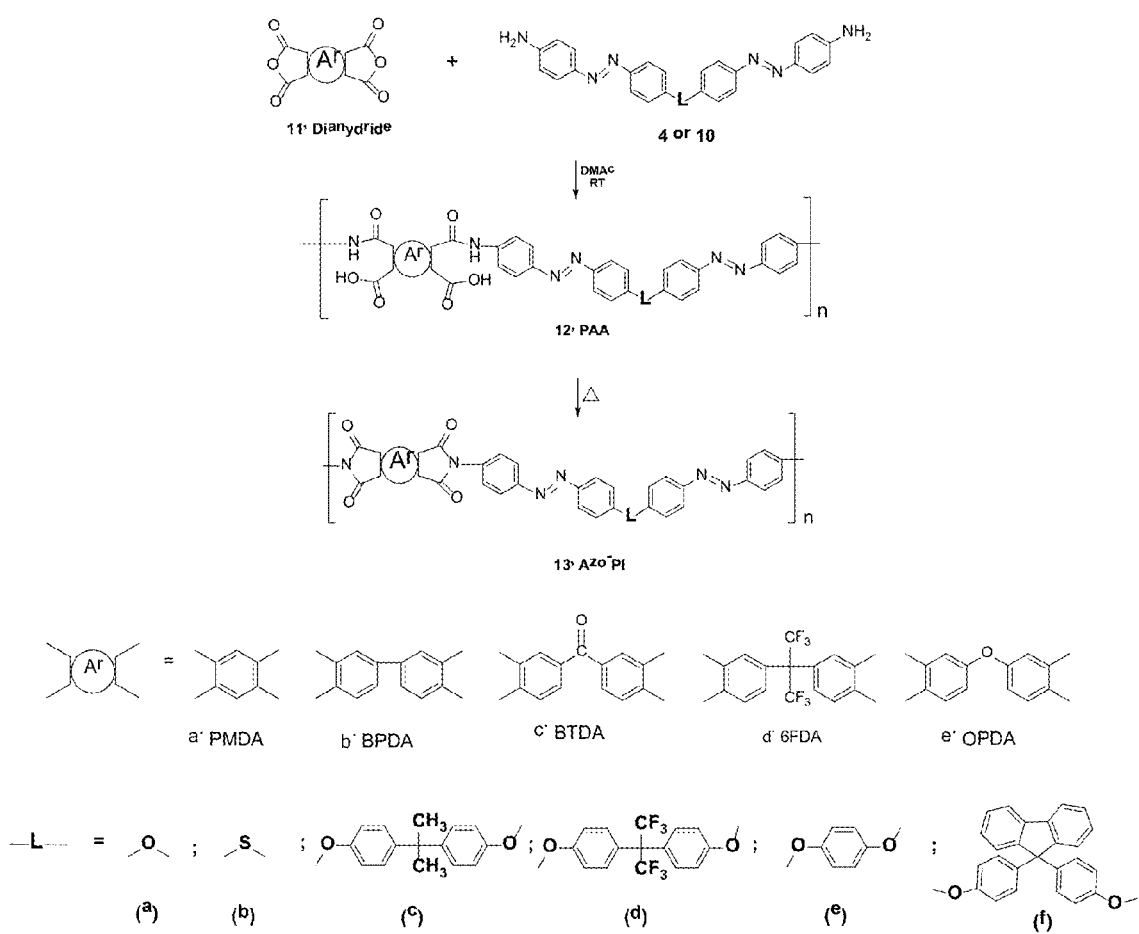
FIG. 3 illustrates an exemplary synthetic scheme toward producing bis(azobenezene)-containing polyimides that incorporate bis(azobenezene)-diamino monomers and various aryl-based dianhydrides, in accordance with another embodiment of the present invention.
Figure 4:
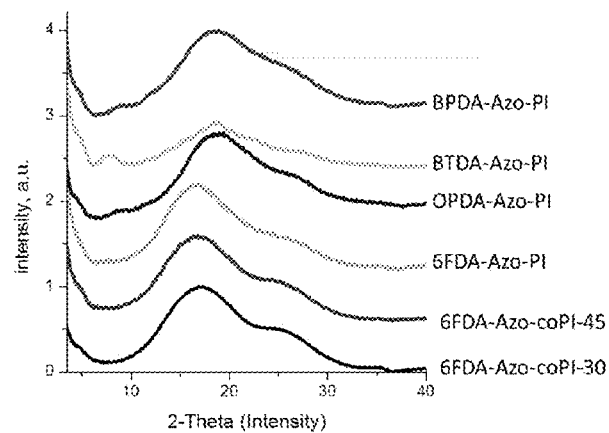
FIG. 4 is a composite of WAXD diffraction traces of various linear azo-polyimides and azo-copolyimides.

Accordingly, novel photomechanically active linear polyimides may be prepared from the bis(azobenzene)-diamino monomers 4a, 4b, and 10a-d and a large collection of readily available dianhydride monomers. As shown in FIG. 3, a general synthesis of bis(azobenzene)-containing polyimides (designated as 13 and Azo-PI) is conducted via a conventional two-step, "poly(amic acid) precursor" (PAA) route. Briefly, a bis(azobenzene)-diamino monomer (4 or 10) and a dianhydride are mixed in an aprotic polar solvent such as N,N-dimethylacetamide (DMAc), N-methylpyrrolidinone (NMP) etc. at room temperature to generate a viscous solution of the corresponding bis(azobenzene)-containing poly(amic acid). After dilution with an appropriate amount of polar solvent, the bis(azobenzene)-containing poly(amic acid) solution was poured into a casting dish, followed by vacuum evaporation of the solvent at 50° C. and a heating schedule to form the bis(azobenzene)-containing polyimide 13. A typical heating schedule includes sequentially heating the bis(azobenzene)-containing poly(amic acid) precursor at about 100° C. for about an hour, at about 150° C. for about an hour, at about 175° C. for about an hour, at about 200° C. for about an hour, at about 250° C. for about an hour, and at about 300° C. for about an hour, to form the bis(azobenzene)-containing polyimides in the form of thin films. In accordance with an embodiment of the present invention, the film thickness of the bis(azobenzene)-containing polyimide film was in a range of about 20 μm to about 100 μm.

In accordance with an embodiment, the dianhydride monomer may include, but is not limited to, pyromellitic dianhydride (PMDA); 3,3',4,4'-biphenyltetracarboxylic dianhydride (BPDA); 3,3',4,4'-benzophenone tetracarboxylic dianhydride (BTDA); 2,2-[bis(4-phthalic anhydrido)]-1,1,1,3,3,3-hexafluoroisopropane (6FDA); 4,4'-oxybis (phthalic anhydride) (OPDA); 3,3',4,4'-diphenylsulfone tetracarboxylic dianhydride; 3,3',4,4'-benzophenone tetracarboxylic dianhydride; 4,4'-(2,2,2-trifluoro-1-phenylethylidene)bis[phthalic anhydride]; 2,2-bis[4-(3,4-dicarboxyphenoxy)phenyl]propane dianhydride; 4,4'-(p-phenylenedioxy) bis[phthalic anhydride]; 4,4'-(m-phenylenedioxy)bis [phthalic anhydride]; 4,4'-(o-phenylenedioxy)bis[phthalic anhydride]; or mixtures thereof. In another embodiment, the dianhydride monomer is selected from the group consisting of pyromellitic dianhydride (PMDA); 3,3',4,4'-biphenyltetracarboxylic dianhydride (BPDA); 3,3',4,4'-benzophenone tetracarboxylic dianhydride (BTDA); 2,2-[bis(4-phthalic anhydrido)]-1,1,1,3,3,3-hexafluoroisopropane (6FDA); and 4,4'-oxybis(phthalic anhydride) (OPDA), which are labeled a-e, respectively, in FIG. 3.

Thus, in accordance with another embodiment of the present invention, the bis(azobenzene)-containing polyimides (designated as 13, in FIG. 3) may be defined by the following general chemical formula (II):

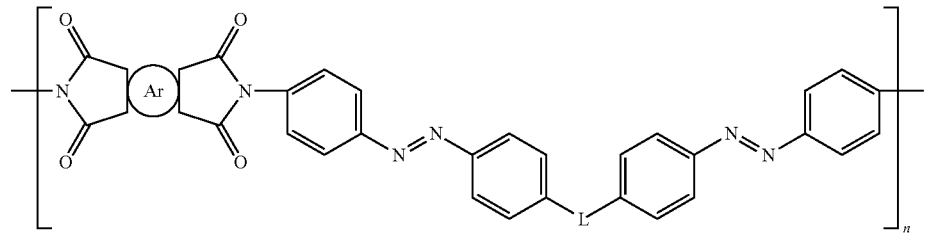

wherein n is a degree of polymerization;
wherein

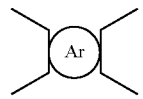

is selected from the group consisting of

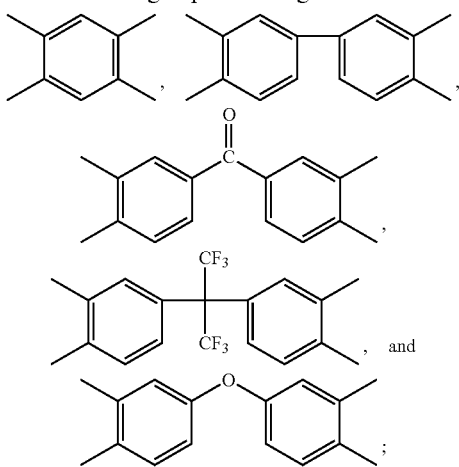

and
wherein -L- is selected from the group consisting of

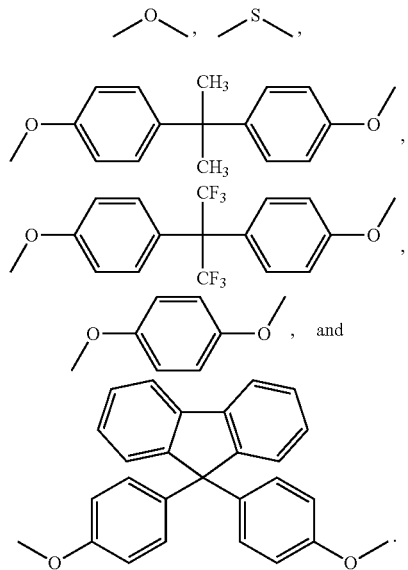

In an embodiment, the degree of polymerization (DP) is in the range of about 50 to about 500. For example, the degree of polymerization may be about 50, about 75, about 100, about 150, about 200, about 250, about 300, about 350, about 400, about 450, or about 500, or in a range between any of the foregoing. DP is the number of repeat units.

FIGS. 4-7, which are discussed in more detail below, provide details about the physical and photomechanical properties of exemplary bis(azobenzene)-containing polyimides.

Copolymerization is a simple and effective way to vary the one or more properties of a polymer system when the resulting properties are linearly correlated to the structure and concentration of the pertinent component of the polymer structures. In the case of photomechanical polymers, it is known that polymer modulus and concentration of chromophores (e.g. azobenzene) are two of the important molecular factors in determining the photomechanical outcome. Accordingly, in yet another embodiment, a bis(azobenzene)-containing copolyimide is provided that includes two different types of diamine monomers, (e.g. a bis(azobenzene)-diamino monomer and a non-azobenzene diamine), which are reacted with about a stoichiometric amount (i.e., about a 1:1 molar ratio) of the dianhydride monomer. The resulting bis(azobenzene)-containing copoly(amic acid) precursor is then converted to the corresponding bis(azobenzene)-containing copolyimide. Depending on the manner of addition, the bis(azobenzene)-containing copolyimide may be characterized as a block copolyimide or a random copolyimide, as further explained below.

Block Copolyimide:

Preparation of a bis(azobenzene)-containing block copolyimide involves a sequential addition of a first diamine monomer (100−x mol %) with a stoichiometric excess (100 mol %) of the dianhydride monomer, which generates an anhydride-terminated poly(amic acid) precursor. After a sufficient period of time to allow the first diamine monomer to be substantially (or partially) consumed, the second diamine monomer (x mol %) is added to the reaction mixture to react with the anhydride end-groups, as well as the remaining dianhydride monomer. The resulting bis(azobenzene)-containing copoly(amic-acid) is converted to the corresponding bis(azobenzene)-containing block copolyimide following the typical thermal imidization protocol. In an embodiment, the first diamine monomer is the non-azobenzene diamine, and the second diamine monomer is the bis(azobenzene)-diamino monomer. In another embodiment, the first diamine monomer is the bis(azobenzene)-diamino monomer, and the second diamine monomer is the non-azobenzene diamine.

In accordance with an embodiment, the non-azobenzene diamine comprises an aromatic diamine, which includes, but is not limited to, 1,3-bis(3-aminophenoxy)benzene (APB); 1,4-bis(3-aminophenoxy)benzene; 1,2-bis(3-aminophenoxy)benzene; 1,2-bis(4-aminophenoxy)benzene; 1,3-bis(4-aminophenoxy)benzene; 1,4-bis(4-aminophenoxy)benzene; 3,4'-oxydianiline; 4,4-oxydianiline; 1,3-diamino-4-methylbenzene; 1,3-diamino-4-(trifluoromethyl)benzene; 2,4-diaminobiphenyl; 2,2-bis(4-aminophenyl)-1,1,1,3,3,3-hexafluoropropane; 2,2-bis(4-aminophenyl)propane; 2,2-bis[4-(4-aminophenoxy)phenyl]-1,1,1,3,3,3-hexafluoropropane; 2,2-bis[4-(4-aminophenoxy)phenyl]propane; or a mixture of thereof.

Figure 8:
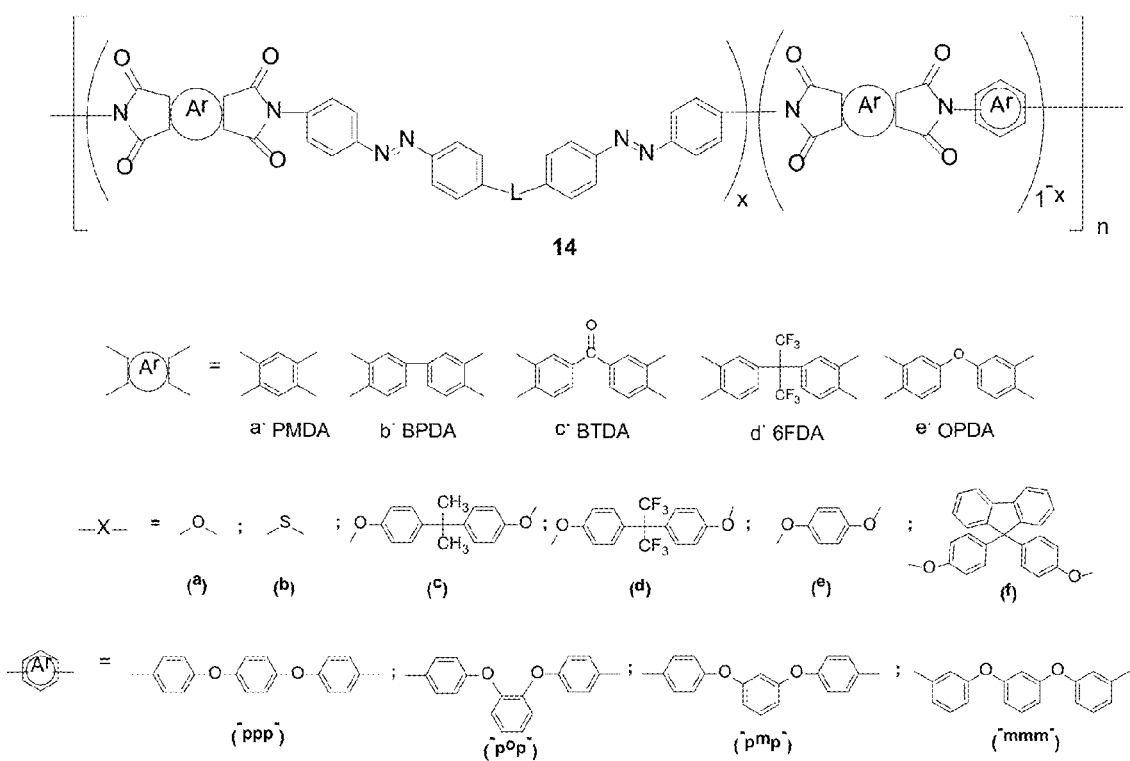
FIG. 8 depicts the general structural representation for both random and block bis(azobenezene)-containing copolyimides that incorporate bis(azobenezene)-diamino monomers, various aryl-based dianhydrides, and various aryl-based diamines, in accordance with another embodiment of the present invention.

In accordance with an embodiment shown in FIG. 8, a block or random bis(azobenzene)-containing copolyimide (14) is provided that includes the bis(azobenzene)-diamino monomer, a dianhydride, and an aryl diamine, and may be defined by a general chemical formula (III):

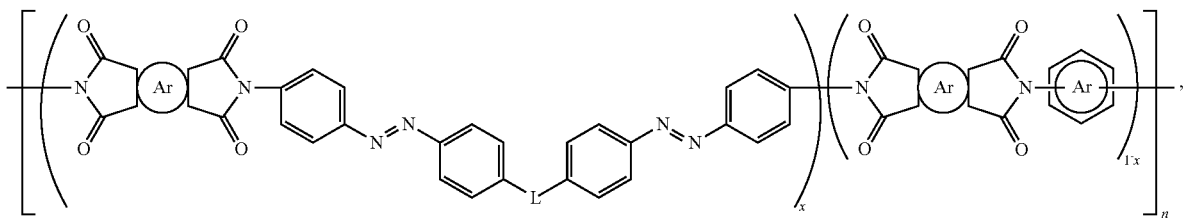

wherein n is a degree of polymerization; wherein x is in a range from about 0.01 to about 0.99;
wherein

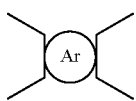

is selected from the group consisting of

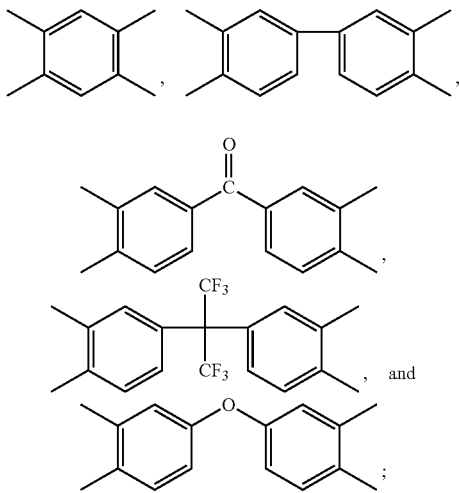

wherein -L- is selected from the group consisting of

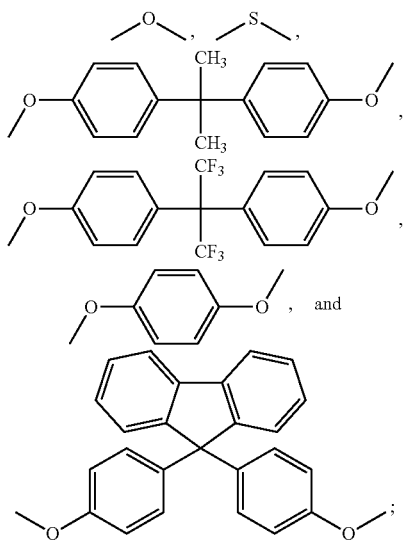

and
wherein

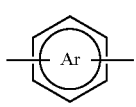

is selected from the group consisting of

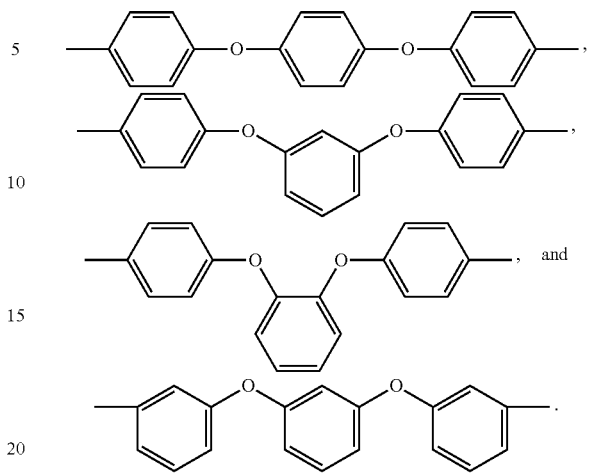

In an embodiment, the degree of polymerization (DP) is in the range of about 50 to about 500. For example, the degree of polymerization may be about 50, about 75, about 100, about 150, about 200, about 250, about 300, about 350, about 400, about 450, or about 500, or in a range between any of the foregoing. DP is the number of repeat units.

To form the desired bis(azobenzene)-containing block copolyimide, x may be in a range from about 0.01 to about 0.99, or in a range from about 0.05 to about 0.95. For example, x may be about 0.01, about 0.05, about 0.10, about 0.15, about 0.20, about 0.25, about 0.30, about 0.35, about 0.40, about 0.45, about 0.50, about 0.55, about 0.60, about 0.65, about 0.70, about 0.75, about 0.80, about 0.85, about 0.90, about 0.95, or about 0.99, or in a range between any of the foregoing. In another embodiment, the bis(azobenzene)-diamino monomer is present in the bis(azobenzene)-containing block copolyimide in an amount from about 1 mol % to about 99 mol %, or about 5 mol % to about 95 mol %. For example, the block bis(azobenzene)-containing copolyimide may comprise about 30 mol %, about 35 mol %, about 45 mol %, or about 70 mol % of the bis(azobenzene)-diamino monomer.

Figure 9:
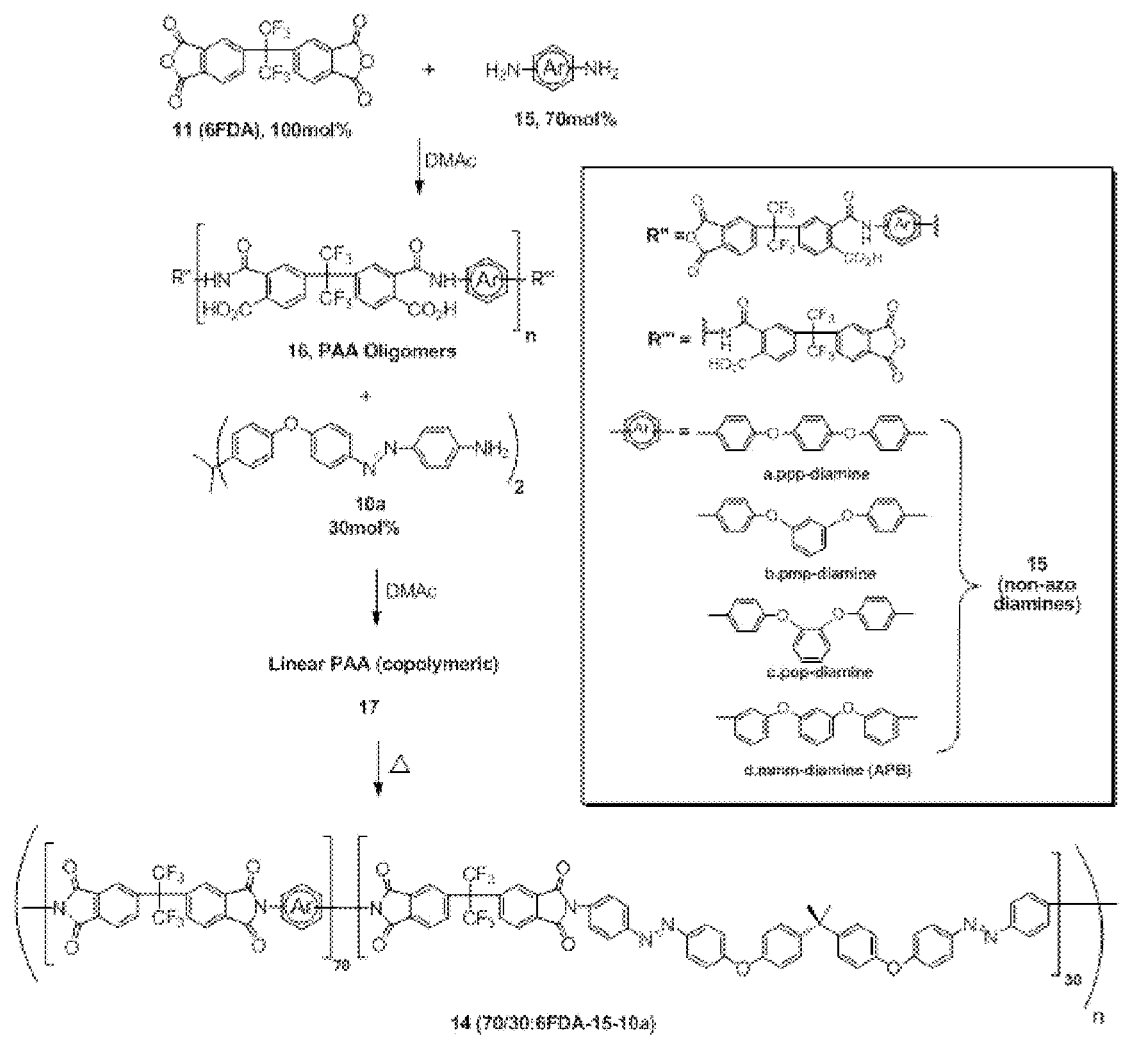
FIG. 9 illustrates an exemplary method for making bis(azobenezene)-containing block copolyimides (e.g., 6FDA-15-10a) containing 70 mol % and 30 mol % of 6FDA-15 and 6FDA-10a polyimide blocks, respectively, using sequential diamine addition, in accordance with another embodiment of the present invention.

As shown in FIG. 9, the preparation of exemplary bis(azobenzene)-containing block copolyimides is illustrated by using a bis(azobenzene) diamine monomer (10a) at 30 mol % and a non-azobenzene diamine (e.g., an aromatic diamine; 15a-d) at 70 mol %, together with the stoichiometric amount (100 mol %) of a dianhydride (e.g. 6FDA in FIG. 3). This is accomplished by using the synthetic tactics involving a sequential addition of the non-azobenzene diamine monomer to first generate an anhydride-terminated poly(amic acid) from the condensation of the dianhydride (in 30 mol % excess) and the non-azobenzene diamine (15a-d), followed by the addition of the bis(azobenzene) diamine to react with anhydride end-groups stoichiometrically. The resulting bis(azobenzene)-containing copoly(amic acid) is converted to the corresponding bis(azobenzene)-containing copolyimide following the typical thermal imidization protocol.

Random Copolyimide:

Preparation of a bis(azobenzene)-containing random copolyimide involves a mixture of diamines comprising the bis(azobenzene)-diamino monomer (x mol %) and the non-azobenzene diamine (100–x mol %), where the diamine mixture is allowed to react simultaneously with a stoichiometric amount (100 mol %) of the dianhydride monomer. The resulting bis(azobenzene)-containing random copoly (amic-acid) is converted to the corresponding bis(azobenzene)-containing random copolyimide following the typical thermal imidization protocol.

To form the desired bis(azobenzene)-containing random copolyimide, x may be in a range from about 0.01 to about 0.99, or in a range from about 0.05 to about 0.95. For example, x may be about 0.01, about 0.05, about 0.10, about 0.15, about 0.20, about 0.25, about 0.30, about 0.35, about 0.40, about 0.45, about 0.50, about 0.55, about 0.60, about 0.65, about 0.70, about 0.75, about 0.80, about 0.85, about 0.90, about 0.95, or about 0.99 or in a range between any of the foregoing. In other words, the bis(azobenzene)-diamino monomer may be present in the bis(azobenzene)-containing random copolyimide in an amount from about 1 mol % to about 99 mol %, or about 5 mol % to about 95 mol %. For example, the bis(azobenzene)-containing random copolyimide may comprise about 30 mol %, about 35 mol %, about 45 mol %, or about 70 mol % of the bis(azobenzene) diamine monomer, as shown in FIG. 10.

Figure 10:
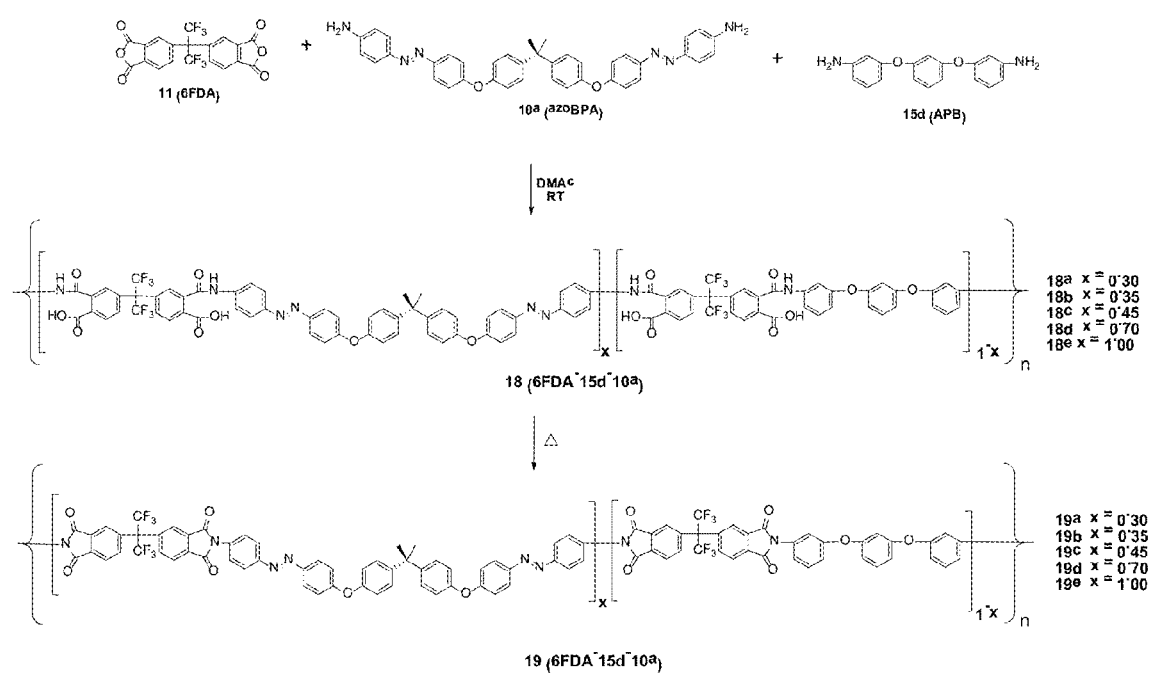
FIG. 10 illustrates an exemplary method for making bis(azobenezene)-containing random copolyimides using a "single mixing of all monomers" procedure, in accordance with another embodiment of the present invention.

With further reference to FIG. 10, the preparation of exemplary bis(azobenzene)-containing random copolyimides is illustrated. Four 6FDA-based copolyimides (19-a-d, labeled as azoBPA-6FDI-xx, where xx stands for the azoBPA content in mol %) were prepared from 6FDA (11), azoBPA (10a) and APB (15d). Briefly, 6FDA (11), azoBPA (10a) and APB (15d) were dissolved under nitrogen atmosphere in N,N-dimethylacetamide (DMAc) at room temperature for 24 h to generate bis(azobenzene)-containing copoly(amic acid) (cPAA, 18a-d). The resulting bis(azobenzene)-containing random cPAA precursor was poured onto glass slides and cured in an oven set to 300° C. to imidize the bis(azobenzene)-containing random copolyimide films. For benchmarking, azoBPA-6FDA homopolymer (13c polyimide) was prepared from 6FDA (11) and azoBPA (10a) in stoichiometric amounts using the same procedure.

Figures 11A, 11B:
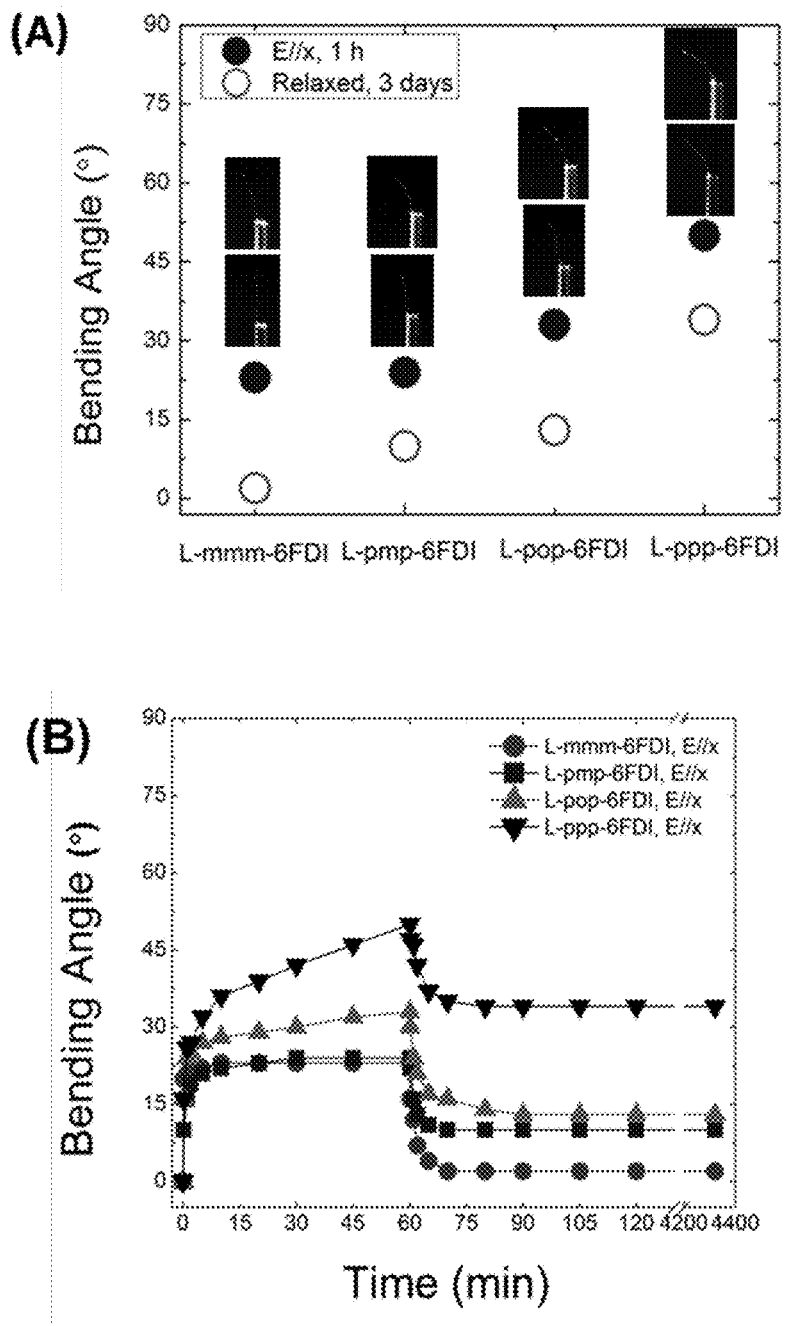
FIG. 11A is a graph showing bending angles at 1 hour light exposure and after 3 days dark relaxation for various linear azo-polyimides.
FIG. 11B is a graph showing time resolved bending angles for various linear azo-polyimides.
Figure 12:
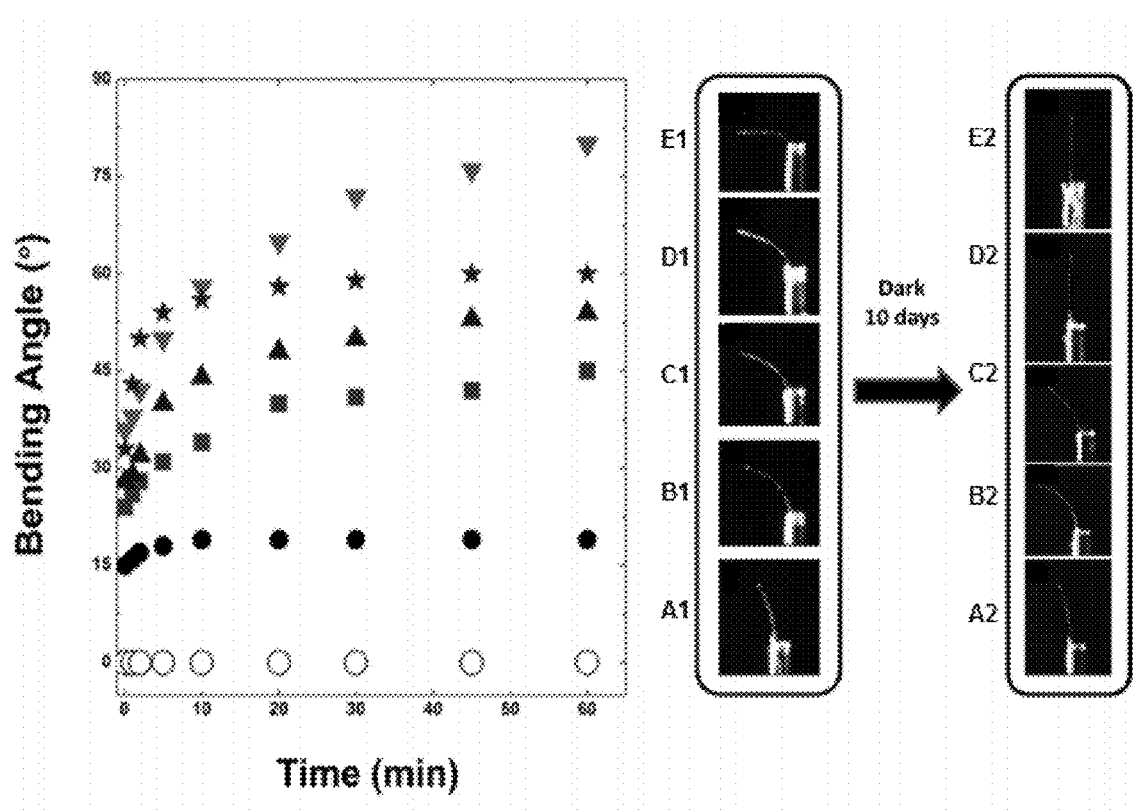
FIG. 12 shows a series of time-resolved measurements of photomechanical responses of 6FDA-coPIs in the changes of bending angle upon exposure to linearly polarized (E//x) 445 nm light at 120 mW/cm² for 1 hour with photographs (A1-E1) taken at 60 min time mark, and photographs (A2-E2) after 10 days relaxation at dark.
Figure 13A:
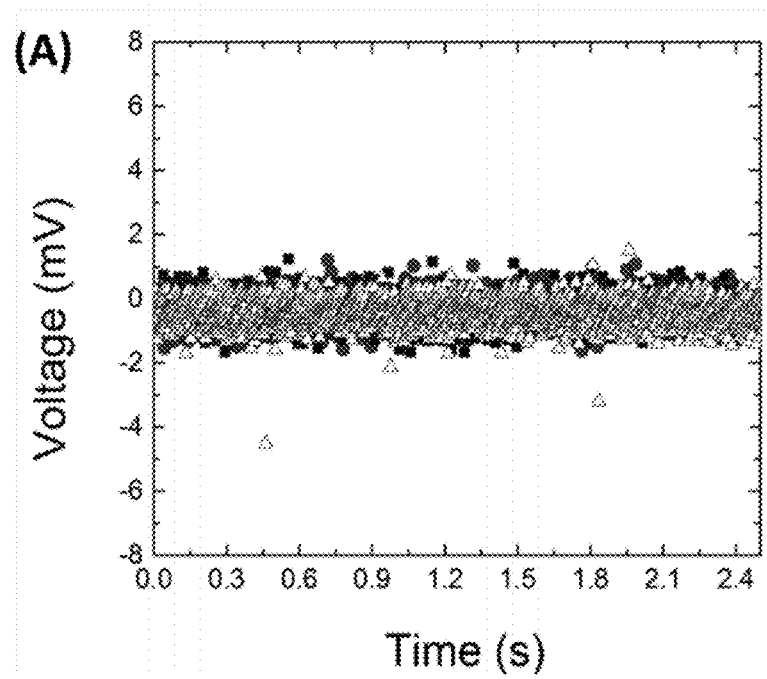
FIGS. 13A-13B are plots of voltage vs. time that show photoinduced piezoelectricity of azoBPA-6FDA with (A) draw ratio of 1 and (B) draw ratio of 3.
Figure 13B:
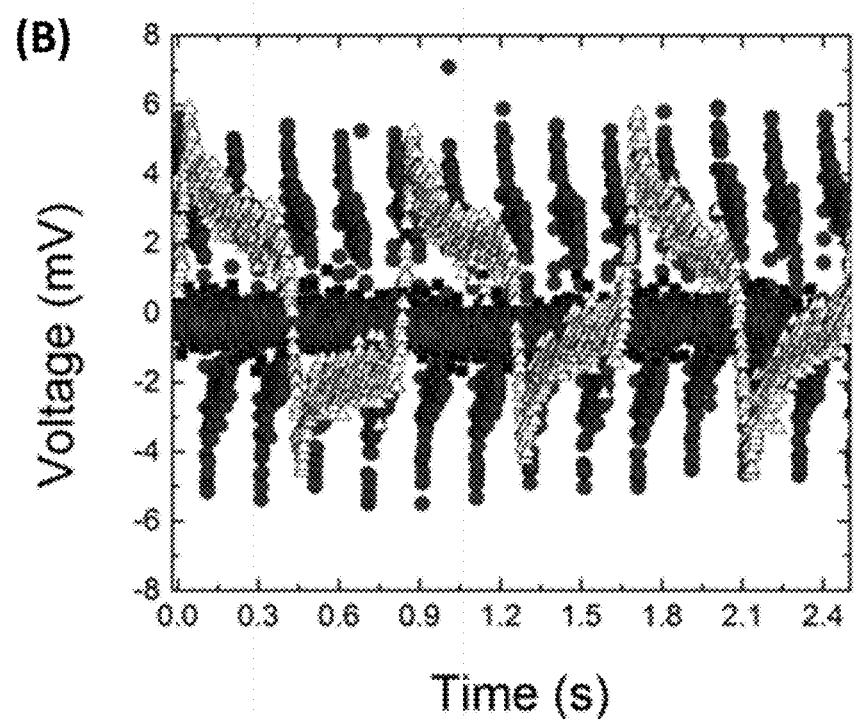

In FIGS. 11-13, which are discussed in more detail below, provide details about the physical and photomechanical properties of exemplary bis(azobenzene)-containing block and random copolyimides.

Polyamides and Poly(amide-imide)s

Synthesis of a bis(azobenzene)-containing polyamide is typically accomplished by two general methods. A first method involves polymerization of the bis(azobenzene) diamine monomer and a diacid halide (e.g., chloride) in about a stoichiometric ratio (i.e., about a 1:1 molar ratio) in an amide solvent such as N,N-dimethylformamide (DMF), N,N-dimethylacetamide (DMAc), N-methylpyrrolidone (NMP), etc. Exemplary diacid halide monomers include, but are not limited to, isophthaloyl chloride; terephthaloyl acid; 4,4'-oxydibenzoyl chloride; 3,4'-oxydibenzoyl chloride; 3,3'-oxydibenzoyl chloride; 4,4'-[2,2,2-trifluoro-1-(trifluoromethyl)ethylidene]bis(benzoyl chloride); 4,4'-(1-methylethylidene) bis(benzoyl chloride); 4,4'-(9H-fluoren-9-ylidene)bis(benzoyl chloride); or a mixture thereof.

A second method of synthesizing the bis(azobenzene)-containing polyamide involves polymerization of the bis (azobenzene) diamine monomer and a dicarboxylic acid with the aid of a promoter/catalyst combination such as triethylphosphite/pyridine (via Yamazaki-Higashi reaction) in an amide solvent such as N,N-dimethylformamide (DMF), N,N-dimethylacetamide (DMAc), N-methylpyrrolidone (NMP), etc. Exemplary dicarboxylic acid monomers include, but are not limited to, isophthalic acid, terephthaloyl acid; 4,4'-oxydibenzoic acid; 3,4'-oxydibenzoic acid; 3,3'-oxydibenzoic acid; 4,4'-[2,2,2-trifluoro-1-(trifluoromethyl)ethylidene]bis(benzoic acid); 4,4'-(1-methylethylidene)bis-benzoic acid; 4,4'-(9H-fluoren-9-ylidene)bis(benzoic acid); or a mixture thereof.

The synthesis of a bis(azobenzene)-containing poly (amide-imide) is typically accomplished by polymerization of i) the bis(azobenzene) diamine monomer and a trimellitic anhydride (TMA) or trimellitic anhydride acid chloride (TMAC); or ii) the bis(azobenzene) diamine monomer and a diimide-dicarboxylic acid monomer derived from a selective condensation of TMA and a diamine (e.g., $H_2N$—Ar—$NH_2$ or the bis(azobenzene) diamine monomer). When acid monomers are used, the polymerization process is aided by triethylphosphite/pyridine (Yamazaki-Higashi reagent) in a 1:1 molar ratio in an amide solvent such as N,N-dimethylformamide (DMF), N,N-dimethylacetamide (DMAc), N-methylpyrrolidone (NMP), etc.

Persons having ordinary skill in the art will appreciate that these polymerization methods may be applied to other dianhydride monomers containing pre-formed aromatic amide moieties. For example, bis(phthalic anhydride) monomers with preformed amide as part of the linking group, which are also known as diamide-dianhydrides, can be prepared from trimellitic anhydride acid chloride (TMAC) and an aromatic diamine (e.g., $H_2N$—Ar—$NH_2$) in refluxing acetone with pyridine as HCl scavenger.

The following examples and methods are presented as illustrative of the present invention or methods of carrying out the invention, and are not restrictive or limiting of the scope of the invention in any manner.

EXAMPLES

Example 1: Synthesis of N-(4-nitrosophenyl)acetamide (2)

After oxone (potassium peroxymonosulfate, from Aldrich; 12.28 g, 20.0 mmol) had dissolved completely in water (100 mL), potassium carbonate (4.14 g, 30 mmol) was added slowly to neutralize the solution to a weak acidity. The solution was added quickly into a solution of 4'-aminoacetanilide (Aldrich; 1.50 g, 10.0 mmol) in water (150 mL). The mixture immediately turned green and then, greenish-gray solids started to fall out of solution. After the mixture had been stirred for another 10 minutes, the precipitates were collected on a filter funnel, air dried, and recrystallized from hot ethanol. Two batches of products were collected to give a total yield of 1.06 g (65%) greenish crystals, m.p. 179-180° C. (lit. 179° C.-180° C.).

Example 2: 4,4'-Oxybis[4-(4-acetamidophenyldiazenyl)phenyl] (3a)

4,4'-Oxydianiline (1a; 4.00 g, 20.0 mmol), N-(4-nitrosophenyl)acetamide (2; 13.1 g, 80.0 mmol) and acetic acid (220 mL) were charged into a 500 mL round-bottomed flask equipped with a magnetic stir bar. The mixture was stirred at room temperature for 48 h. The mixture was filtered to afford a yellow solid, which was washed with acetic acid followed by of ethanol. The raw product was recrystallized from DMAc to afford 5.32 g (53%) of 4,4'-oxybis[4-(4-acetamidophenyldiazenyl)phenyl] (3a) as yellow crystals, m.p.>300° C. IR (KBr, cm$^{-1}$): 3260 (NHCO), 3065, 1660 (C=O), 1589, 1542, 1523, 1491, 1404, 1369, 1263, 1149, 1100, 1008, 842, 586, 550. $^1$-NMR (d$_6$-DMSO, δ in ppm): 2.09 (s, 6H, COCH$_3$), 7.27-7.29 (d, 4H, Ar—H), 7.78-7.94 (m, 12H, Ar—H), 10.28 (s, 2H, NHCO). $^{13}$C-NMR (d6-DMSO, δ in ppm): 24.12, 119.11, 119.50, 123.53, 124.45, 142.26, 147.39, 148.34, 158.20, 168.76. Anal. Calcd. for $C_{28}H_{24}N_6O_3$: C, 68.28%, H, 4.91%, N, 17.06%, Found: C, 68.27%, H, 4.87%, N, 16.30%.

Example 3: 4,4'-Oxybis[4-(4-aminophenyldiazenyl)phenyl] (Azo-ODA, 4a)

To a 500 mL round-bottomed flask with a stir-bar and a condenser, 4,4'-oxybis[4-(4-acetamidophenyldiazenyl)phenyl] (3a; 2.90 g, 5.88 mmol), 6 M HCl (40 mL) and ethanol (160 mL) were charged and heated to 105° C. for 48 h. After it was allowed to cool to room temperature, DI water (600 mL) was added. The resulting red solid was collected by filtration and washed with 1N sodium hydroxide solution, followed by deionized water. The product was dried in a vacuum oven to afford 2.34 g (98%) of orange red solid, m.p. 182.2-183.4° C. IR (KBr, cm$^{-1}$): 3544, 3385 (NH$_2$), 3038, 1579, 1487, 1241, 1147, 1097, 840, 510. $^1$H-NMR (d$_6$-DMSO, δ in ppm): 6.04 (s, 4H, NH2), 6.65-6.68 (d, 4H, Ar—H), 7.18-7.21 (d, 4H, Ar—H), 7.63-7.65 (d, 4H, Ar—H), 7.79-7.81 (d, 4H, Ar—H). $^{13}$C-NMR (d$_6$-DMSO, δ in ppm): 113.37, 119.21, 123.55, 124.94, 142.79, 148.64, 152.61, 157.17. Anal. Calcd. for C24H20N6O: C, 70.57%; H, 4.94%; N, 20.58%. Found: C, 70.39%; H, 4.89%; N, 20.43%.

Example 4: 4,4'-Thiobis[4-(4-acetamidophenyldiazenyl)phenyl] (3b)

Bis(4-aminophenyl)sulfide (1b; 1.00 g, 4.62 mmol), N-(4-nitrosophenyl)acetamide (2; 3.06 g, 18.49 mmol) and acetic acid (55 mL) were charged into a 250 mL round-bottomed flask equipped with a magnetic stir bar. The mixture was stirred at room temperature for 48 h. The mixture was filtered to afford a yellow solid, which was washed with acetic acid followed by of ethanol. The raw product was recrystallized from DMAc to afford 1.54 g (66%) of yellow crystals, m.p.>350° C. IR (KBr, cm$^{-1}$): 3291, 1658, 1591, 1516, 1406, 1366, 1301, 1259, 1151, 1107, 1079, 1009, 841, 766, 730, 628, 586, 549. $^1$H-NMR (d$_6$-DMSO, δ in ppm): 2.09 (s, 6H, COCH$_3$), 7.54-7.56 (d, 4H, Ar—H), 7.78-7.87 (dd, 12H, Ar—H), 10.30 (s, 2H, NHCO). $^{13}$C-NMR (d$_6$-DMSO, δ in ppm): 24.12, 119.09, 123.45, 123.75, 131.37, 137.44, 142.58, 147.39, 151.07, 168.79. Anal. Calcd. for $C_{28}H_{24}N_6O_2S$: C, 66.12%, H, 4.76%, N, 16.52%, Found: C, 66.21%, H, 4.78%, N, 15.52%.

Example 5: 4,4'-Thiobis[4-(4-aminophenyldiazenyl) phenyl] (azoBPS, 4b)

4,4'-Thiobis[4-(4-acetamidophenyldiazenyl)phenyl] (3b; 1.00 g, 1.966 mmol), hydrochloric acid (6 N, 40 mL) and ethanol (4 mL) were charged into a 250 mL round-bottomed flask equipped with a magnetic stir bar. The mixture was stirred at 120° C. for 48 h. The mixture was filtered to afford a brown solid. It was then washed with water followed by a 1N NaOH solution followed by another water rinse. The product was dried in vacuum oven at 80° C. overnight to afford 0.54 g (65%) of brown solid. m.p.: 186-188.6° C. IR (KBr, cm$^{-1}$): 3547, 3386, 3319, 3199, 1597, 1580, 1497, 1475, 1426, 1397, 1259, 1138, 1076, 1006, 953, 841, 729, 689, 641, 543. $^1$H-NMR (d$_6$-DMSO, δ in ppm): 6.15 (s, 4H, NH$_2$) 6.65 (d, 4H, Ar—H), 7.47 (d, 4H, Ar—H), 7.64 (d, 4H, Ar—H), 7.74 (d, 4H, Ar—H). $^{13}$C-NMR (d6-DMSO, δ in ppm): 113.41, 122.80, 125.33, 131.31, 135.62, 142.85, 151.56, 153.69. Anal. Calcd. for $C_{24}H_{20}N_6S$: C, 67.90%, H, 4.75%, N, 19.80%, Found: C, 67.67%, H, 4.62%, N, 17.81%.

Example 6: 2,2-Bis[4-(4-nitrophenoxy)phenyl]propane (7a)

Into a 1 L three-necked flask equipped with a magnetic stir bar and nitrogen inlet and outlet were placed 2,2-bis(4-hydroxyphenyl)propane (5a) (18.0 g, 79.0 mmol), 4-fluoronitrobenzene (6) (25.0 g, 180 mmol), potassium carbonate (24.5 g, 180 mmol), and DMF (300 mL). The mixture was stirred at room temperature for 24 h and filtered. Filtrate was diluted with ethyl acetate (1200 mL) and the organic layer was separated. The organic layer was washed three times with water, then dried with magnesium sulfate and filtered. The filtrate was evaporated to afford yellowish crystals, which recrystallized from methanol/ethyl acetate to yield 18.33 g (61%) of off-white crystals; m.p. 120.0-121.2° C. IR (KBr, cm$^{-1}$): 3446, 3072, 2971, 2877, 2451, 1904, 1610 (NO$_2$), 1344 (NO$_2$), 1249 (ether). NMR (DMSO-d$_6$, δ in ppm) 1.70 (s, 6H, CH$_3$), 7.11-7.14 (m, 8H, Ar—H), 7.35-7.38 (m, 4H, Ar—H), 8.23-8.27 (m, 4H, Ar—H). MS (m/z) 470 (M$^+$). Anal. Calcd. for $C_{27}H_{23}N_2O_6$: C, 68.80%; H, 4.89%; N, 6.01%. Found: C, 69.52%; H, 4.76%; N, 5.70%.

Example 7: 2,2-Bis[4-(4-aminophenoxy)phenyl]propane (8a)

2,2-Bis[4-(4-nitrophenoxy)phenyl]propane (7a; 5.0 g, 10.6 mmol) dissolved in ethyl acetate (100 mL) and palladium on activated carbon (0.30 g) was placed in a hydrogenation bottle. The bottle was tightly secured on a Parr hydrogenation apparatus, flushed four times with hydrogen, pressurized to 55 psi. After the mixture had been agitated at room temperature for 24 h under the hydrogen pressure of 55 psi, it was filtered through Celite. The filter cake was washed with ethyl acetate, and then the filtrate was evaporated to dryness on a rotary evaporator to afford 4.214 g (95%) of off-white crystals; m.p. 126.5-127.5° C. IR (KBr, cm$^{-1}$): 3423, 3402, 3333, 3235 (amine), 3038, 2964, 2869, 1879, 1733, 1610, 1498, 1222 (ether), 872. $^1$H NMR (DMSO-d$_6$, δ in ppm): 1.55 (s, 6H, CH$_3$), 4.94 (s, 4H, NH$_2$), 6.55-6.71 (m, 4H, Ar—H), 6.71-6.77 (m, 8H, Ar—H), 7.11-7.13 (m, 4H, Ar—H). Anal. Calcd. for $C_{27}H_{26}N_2O_2$: C, 79.00%, H, 6.38%, N, 6.82%, Found: C, 78.27%, H, 6.65%, N, 6.45%.

Example 8: 2,2-Bis{4-[4-(4-acetamidophenyldiazenyl)phenoxy]phenyl} propane (9a)

2,2-Bis[4-(4-aminophenoxy)phenyl]propane (8a; 0.821 g, 2.00 mmol), N-(4-nitrosophenyl)acetamide (2; 1.312 g, 8 mmol) and acetic acid (40 mL) were charged into a 150 mL round-bottomed flask equipped with a magnetic stir bar. The mixture was stirred at room temperature for 48 h. The mixture was at first turned into a greenish solution, and then yellow particles started to precipitate out of the solution. The mixture was diluted by deionized water (100 mL). Solids were collected and washed with water (500 mL) followed by of ethanol (200 mL) to remove most of the unreacted nitroso reagent. The raw product was slurried in hot ethanol (50 mL) and filtered after cooled to room temperature twice to give 0.91 g (65%) of yellow solids, mp 267.2-269.1° C. (dec.). IR (KBr, cm$^{-1}$): 3320 (NHCO), 3062, 2964, 1674 (C=O), 1594, 1503, 1489, 1238, 1115, 849. MS (m/e): 702 (M$^+$). $^1$H-NMR (d$_6$-DMSO, δ in ppm): 1.67 (s, 6H, COCH$_3$), 2.08 (s, 6H, CCH$_3$) 7.05-7.13 (dd, 8H, Ar—H), 7.30-7.32 (d, 4H, Ar—H), 7.77-7.88 (m, 12H, Ar—H), 10.27 (s, 2H, NHCO). $^{13}$C-NMR (d$_6$-DMSO, δ in ppm): 24.12, 30.57, 41.84, 118.23, 119.08, 123.43, 124.36, 128.26, 142.10, 146.16, 147.37, 147.65, 153.32, 159.37, 168.72. Anal. Calcd. for C$_{43}$H$_{38}$N$_6$O$_4$: C, 73.49%, H, 5.45%, N, 11.96%, Found: C, 73.33%, H, 5.37%, N, 11.70%.

Example 9: 2,2-Bis{4-[4-(4-aminophenyldiazenyl) phenoxy]phenyl}propane (azoBPA, 10a)

To a 500 mL round-bottomed flask with a stir-bar and a condenser, 2,2-bis{4-[4-(4-acetamidophenyldiazenyl)phenoxy]phenyl}propane (9a; 5.00 g, 7.11 mmol), 6 M HCl (200 mL) and 95% ethanol (20 mL) were charged and heated to 105° C. for 48 h. After it was allowed to cool to room temperature, water (600 mL) was added. The resulting red solid was collected by filtration and washed with 1N sodium hydroxide solution, followed by deionized water (300 mL). After air dried, the crude product was purified by column chromatography (silica gel, ethyl acetate as eluent). The solvent was removed by a rotary evaporator to afford 2.95 g (67%) of orange red solid, mp 162.0-163.1° C. IR (KBr, cm$^{-1}$): 3467, 3381 (NH$_2$), 3036, 2964, 1619, 1598, 1505, 1489, 1238, 1145, 834. MS (m/e): 618 (M$^+$). $^1$H-NMR (d$_6$-DMSO, δ in ppm): 1.66 (s, 6H, CCH$_3$), 6.03 (s, 4H, NH$_2$), 6.64-6.66 (d, 4H, Ar—H), 7.01-7.03 (d, 4H, Ar—H), 7.07-7.09 (d, 4H, Ar—H), 7.28-7.30 (d, 4H, Ar—H), 7.61-7.63 (d, 4H, Ar—H), 7.75-7.77 (d, 4H, Ar—H). $^{13}$C-NMR (d$_6$-DMSO, δ in ppm): 30.54, 41.73, 113.31, 118.41, 118.64, 123.45, 124.85, 128.12, 142.72, 145.77, 148.15, 152.49, 153.73, 157.87. Anal. Calcd. for C$_{39}$H$_{34}$N$_6$O$_2$: C, 75.71%; H, 5.54%; N, 13.58%. Found: C, 75.62%; H, 5.39%; N, 13.48%.

Example 10: 2,2-Bis{4-[4-(4-acetamidophenyldiazenyl)phenoxy]phenyl}hexafluoropropane (9b)

2-Bis[4-(4-aminophenoxy)phenyl]hexafluoropropane (8b, 2.00 g, 3.86 mmol), N-(4-nitrosophenyl)acetamide (2; 2.53 g, 15.4 mmol) and acetic acid (110 mL) were charged into a 500 mL round-bottomed flask equipped with a magnetic stir bar. The mixture was stirred at room temperature for 48 h. The mixture was filtered to afford a yellow solid, which was washed with acetic acid followed by of ethanol. The raw product was recrystallized from DMAc to afford 1.53 g (48%) of compound 9b as yellow crystals, m.p. 263.7-264.8° C. (dec.). IR (KBr, cm$^{-1}$): 3297 (NHCO), 3056, 1661 (C=O), 1592, 1540, 1509, 1493, 1407, 1373, 1239, 1206, 1168, 1097, 965, 957, 939, 927, 844, 829, 543, 528. 1H-NMR (d$_6$-DMSO, δ in ppm): 2.09 (s, 6H, COCH3), 7.21-7.27 (dd, 8H, Ar—H), 7.41-7.43 (d, 4H, Ar—H), 7.78-7.93 (d, 12H, Ar—H), 10.28 (s, 2H, NHCO). $^{13}$C-NMR (d6-DMSO, δ in ppm): 24.11, 118.67, 119.09, 119.65, 123.52, 124.43, 127.28, 131.67, 142.26, 147.36, 148.42, 156.84, 157.79, 168.74. Anal. Calcd. for C$_{43}$H$_{32}$F$_6$N$_6$O$_4$: C, 63.70%; H, 3.98%; N, 10.37%; Found: C, 63.73%, H, 4.01%, N, 10.40%.

Example 11: 2,2-Bis{4-[4-(4-aminophenyldiazenyl) phenoxy]phenyl} hexafluoropropane (azo6F,10b)

To a 500 mL round-bottomed flask with a stir-bar and a condenser, 2,2-bis{4-[4-(4-acetamidophenyldiazenyl)phenoxy]phenyl}hexafluoropropane (9b; 1.25 g, 1.54 mmol), 6 M HCl (80 mL) and 95% ethanol (8 mL) were charged and heated to 105° C. for 48 h. After it was allowed to cool to room temperature, water (150 mL) was added. The resulting red solid was collected by filtration and washed with 1N sodium hydroxide solution, followed by deionized water (300 mL). After air dried, the crude product was purified by column chromatography (silica gel, ethyl acetate as eluent). The solvent was removed by a rotary evaporator to afford 0.94 g (84%) of orange red solid, mp 138.2-139.7° C. IR (KBr, cm$^{-1}$): 3386, 3214 (NH$_2$), 3043, 1620, 1595, 1506, 1490, 1240, 1202, 1171, 1145, 967, 928, 830, 704, 542. $^1$H-NMR (d$_6$-DMSO, δ in ppm): 6.07 (s, 4H, NH2), 6.65-6.67 (d, 4H, Ar—H), 7.16-7.23 (m, 8H, Ar—H), 7.38-7.40 (d, 4H, Ar—H), 7.62-7.65 (d, 4H, Ar—H), 7.79-7.81 (d, 4H, Ar—H). $^{13}$C-NMR (d$_6$-DMSO, δ in ppm): 113.37, 118.24, 119.85, 123.61, 125.03, 126.93, 131.60, 142.76, 148.99, 152.73, 156.32, 157.28. Anal. Calcd. for C39H28F6N6O2: C, 64.46%; H, 3.88%; N, 11.57%. Found: C, 64.25%; H, 3.90%; N, 11.54%.

Example 12: 1,4-Bis[4-(4-acetamidophenyldiazenyl) phenoxy]benzene (9c)

1,4-Bis(4-aminophenoxy)benzene (8c; 1.00 g, 3.42 mmol), N-(4-nitrosophenyl)acetamide (2.25 g, 13.68 mmol) and acetic acid (35 mL) were charged into a 100 mL; round-bottomed flask equipped with a magnetic stir bar. The mixture was stirred at room temperature for 48 h. The mixture was filtered to afford a yellow solid, which was washed with acetic acid followed by of ethanol. The raw product was recrystallized from DMAc to afford 1.23 g (62%) of yellow crystals, m.p.>300° C. IR (KBr, cm$^{-1}$): 3258 (NHCO), 3195, 3128, 3065, 1660 (C=O), 1587, 1541, 1524, 1489, 1402, 1365, 1302, 1218, 1189, 1098, 849, 835, 547. $^1$H-NMR (d$_6$-DMSO, δ in ppm): 2.09 (s, 6H, COCH3), 7.17-7.19 (d, 4H, Ar—H), 7.23 (s, 4H, Ar—H), 7.77-7.85 (m, 8H, Ar—H), 7.89-7.91 (d, 4H, Ar—H), 10.28 (s, 2H, NHCO). 13C-NMR (d$_6$-DMSO, δ in ppm): 24.12, 118.10, 119.08, 121.52, 123.44, 147.52, 147.52, 148.34, 151.83, 159.62, 163.22, 168.77.

Example 13:
1,4-Bis[4-(4-aminophenyldiazenyl)phenoxy]benzene (azoBPO, 10c)

To a 250 mL round-bottomed flask with a stir-bar and a condenser, 4,4'-oxybis[4-(4-acetamidophenyldiazenyl)phenyl] (9c; 1.00 g, 1.71 mmol), 6 M HCl (16 mL) and sulfolane (50 g) were charged and heated to 125° C. for 48 h. After it was allowed to cool to room temperature, DI water (600 mL) was added. The resulting red solid was collected by filtration and washed with 1N sodium hydroxide solution, followed by deionized water. It was dried in a vacuum oven to afford 0.78 g (92%) of orange red solid. m.p. 235.9-236.6° C. (dec.). IR (KBr, cm$^{-1}$): 3566, 3416, 3326 (NH$_2$), 3028, 1589, 1489, 1239, 1191, 1150, 1097, 1006, 953, 835, 545, 481. 1H-NMR (d$_6$-DMSO, δ in ppm): 6.04 (s, 4H, NH2), 7.17-7.19 (d, 4H, Ar—H), 7.31-7.34 (d, 4H, Ar—H), 7.63-7.65 (d, 4H, Ar—H), 7.76-7.80 (t, 8H, Ar—H). $^{13}$C-NMR (d$_6$-DMSO, δ in ppm): 113.81, 118.17, 121.06, 123.49, 124.85, 142.80, 148.17, 151.98, 152.37, 158.19.

Example 14:
9,9-Bis[4-[4-(4-nitrophenoxy]phenyl]fluorene (7d)

(9,9-Bis(4-hydroxyphenyl)fluorene, (7d; 15.00 g, 42.8 mmol), 1-Fluoro-4-nitro benzene (6; 14.07 g, 99.7 mmol), potassium carbonate (16.5 g, 119 mmol) and DMF (50 mL) were charged into a 250 mL round-bottomed flask equipped with magnetic stir bar, and a condenser. The mixture was heated at 100° C. for 4 hr. The temperature was raised to 160° C. for 12 hr. The mixture was then allowed to cool, filtered and washed with water. The product was then recrystallized in DMF to afford 24.67 g (70%). m.p.: 344.6-348.3° C. IR (KBr, cm$^{-1}$): 3079, 3039, 1924, 1583, 1484, 1467, 1335, 1247, 1226, 1161, 1110, 1014, 878, 844, 794, 641, 601, 538. $^1$H-NMR (d$_6$-DMSO, δ in ppm): 7.10 (m, 8H, Ar—H), 7.23 (d, 4H, Ar—H), 7.35 (t, 2H, Ar—H), 7.43 (t, 2H, Ar—H), 7.49 (d, 2H, Ar—H), 7.95 (d, 2H, Ar—H), 8.25 (d, 4H, Ar—H).

Example 15:
9,9-Bis[4-[4-(4-aminophenoxy]phenyl]fluorene (8d)

9,9-Bis[4-(4-nitrophenoxy]phenyl)fluorene (7d; 4.00 g, 6.75 mmol), palladium on activated carbon (0.1 g) were charged into a 250 mL round-bottomed flask equipped with magnetic stir bar. The mixture was dissolved in ethanol (54 mL) and heated to 85° C. Hydrazine monohydrate (25 mL) was added dropwise via addition funnel over one hour. After addition of hydrazine was complete, the reaction was heated to reflux at 125° C. for 48 hours. It was then hot filtered and allowed to cool to room temperature. The white crystals was collected by filtration and dried in an oven to afford 2.28 g (63.5%) of product. m.p.: 178.3° C. IR (KBr, cm$^{-1}$): 3472, 3369, 3042, 1618, 1494, 1465, 1229, 1169, 1116, 1011, 917, 873, 824, 749, 628, 558, 499. $^1$H-NMR (d$_6$-DMSO, δ in ppm): 4.92 (s, 4H, NH$_2$), 6.53 (d, 4H, Ar—H), 6.70 (d, 8H, Ar—H), 7.0 (d, 4H, Ar—H), 7.29 (d, 2H, Ar—H), 7.35 (d, 4H, Ar—H), 7.87 (d, 2H, Ar—H). $^{13}$C-NMR (d$_6$-DMSO, δ in ppm): 63.63, 114.77, 115.97, 120.42, 120.90, 125.88, 127.50, 127.78, 128.81, 138.71, 139.31, 145.22, 145.45, 150.94, 157.67.

Example 16:
9,9-Bis[4-[4-(4-acetamidophenyldiazenyl)phenoxy] phenyl]fluorene (9d)

9,9-Bis[4-(4-aminophenoxy)phenyl]fluorene (8d; 1.00 g, 1.87 mmol), N-(4-nitrosophenyl)acetamide (2; 1.23 g, 7.51 mmol), acetic acid (55 mL) were charged into a 250 mL round-bottomed flask equipped with magnetic stir bar. The mixture was stirred for 48 hours under nitrogen. The product was then filtered and washed with acetic acid followed by ethanol. The product was dried to afford 1.13 g (73%). m.p.: 191.3-191.4° C. IR (KBr, cm$^{-1}$): 3311, 3067, 1659, 1489, 1471, 1406, 1372, 1305, 1267, 1150, 1131, 1014, 835, 753, 593, 548. $^1$H-NMR (d$_6$-DMSO, δ in ppm): 2.07 (s, 6H, COCH$_3$), 7.03 (d, 4H, Ar—H), 7.12 (d, 4H, Ar—H), 7.20 (d, 4H, Ar—H), 7.38 (m, 6H, Ar—H), 7.85 (m, 12H, Ar—H), 7.94 (d, 2H, Ar—H), 10.25 (s, 2H, NHCO). $^{13}$C-NMR (d$_6$-DMSO, δ in ppm): 24.11, 63.95, 118.53, 119.12, 119.24, 120.63, 123.44, 124.36, 126.01, 127.85, 128.05, 129.43, 139.47, 141.33, 142.12, 147.41, 147.83, 150.51, 154.44, 159.00, 168.77. Anal. Calcd. for: C, 77.17%, H, 4.89%, N, 10.19%, Found: C, 76.65%, H, 4.78%, N, 9.37%.

Example 17: 9,9-Bis[4-[4-(4-aminophenyldiazenyl) phenoxy]phenyl]fluorene (azoCBO, 10d)

9,9-Bis[4-[4-(4-acetamidophenyldiazenyl)phenoxy]phenyl]fluorene (9d; 1.00 g, 1.21 mmol), 6M hydrochloric acid (40 mL), ethanol (4 mL), were charged into a 250 mL round-bottomed flask equipped with magnetic stir bar. The mixture was stirred, heated to 125° C. for 48 hours. It was then washed with water followed by a 1N NaOH solution followed by another water rinse. It was dried in vacuum oven at 80° C. overnight to afford 0.69 g (76%). m.p.: 179.5-180.6° C. IR (KBr, cm$^{-1}$): 3489, 3392, 3236, 3059, 1597, 1488, 1471, 1450, 1423, 1237, 1145, 1015, 832. 1H-NMR (d$_6$-DMSO, δ in ppm): 6.02 (s, 4H, NH$_2$), 6.64 (d, 4H, Ar—H), 6.99 (d, 4H, Ar—H), 7.07 (d, 4H, Ar—H), 7.17 (d, 4H, Ar—H), 7.34 (t, 2H, Ar—H), 7.40 (t, 2H, Ar—H), 7.48 (d, 2H, Ar—H), 7.60 (d, 4H, Ar—H), 7.73 (d, 4H, Ar—H), 7.94 (d, 2H, Ar—H). $^{13}$C-NMR (d6-DMSO, δ in ppm):63.92, 113.39, 118.75, 118.84, 120.62, 123.51, 124.93, 126.01, 127.82, 128.04, 129.36, 139.46, 140.98, 142.78, 148.37, 150.59, 152.58, 154.89, 157.54. Anal. Calcd. for: C, 79.44%, H, 4.90%, N, 11.34%, Found: C, 79.28%, H, 4.85%, N, 9.91%.

Example 18: Procedure for the Preparation of azoBPA-PMDA Polyimide 2,2-Bis{4-[4-(4-aminophenyldiazenyl)phenoxy] phenyl}propane (10a; 7; 0.3184 g, 0.5246 mmol) and DMAc (4 mL) were added to a 25 mL 3-necked flask equipped with a magnetic stirrer, nitrogen inlet and outlet, and stirred under dry nitrogen at room temperature for 30 min. PMDA (8a; 0.1122 g, 0.5246 mmol) was then charged. The dark red solution was agitated at room temperature for 24 hr to afford a viscous poly(amic acid) solution. This solution was diluted with DMAc (3 mL), poured into a glass dish, followed by vacuum evaporation of DMAc at 50° C., and heat-treated at: 100° C./2 h, 150° C./2 h, 175° C./1 h, 200° C./2 h, 250° C./1 h and 300° C./1 h to form imidized polymers. The film thickness was approximately 20-100 μm. FT-IR (KBr, cm$^{-1}$): 3049 (Ar—H), 2965 (CH$_3$), 1777, 1719 (imide), 1587, 1488, 1356, 1232, 1169, 1113, 1080, 1012, 821, 722, 546.

Example 19: Procedure for the Preparation of azoBPA-6FDA Polyimide

The azoBPA-6FDA polyimide was prepared from 2,2-bis{4-[4-(4-aminophenyldiazenyl)phenoxy]phenyl}propane (10a; 0.5087 g, 0.822 mmol), 6FDA (11d; 0.3652 g, 0.822 mmol) and DMAc (5.5 mL) using the same procedures as the preparation of azoBPA-PMDA polyimide. The film thickness was approximately 20-100 μm. FT-IR (KBr, cm$^{-1}$): 3052 (Ar—H), 2966 (CH$_3$), 1785, 1722 (imide), 1589, 1489, 1411, 1232, 1207, 1191, 1138, 1080, 1012, 834, 720, 548.

Example 20: Procedure for the Preparation of azoODA-6FDA 4,4'-Oxybis[4-(4-aminophenyldiazenyl)phenyl] (4a; Azo-ODA, 0.8000 g, 1.950 mmol) and DMAc (8 mL) were added to a 25 mL 3-necked flask equipped with a magnetic stirrer, nitrogen inlet and outlet, and stirred under dry nitrogen at room temperature for 30 min. 6FDA (11d; 0.8702 g, 1.950 mmol) was then charged. The dark red solution was agitated at room temperature for 24 h to afford a viscous poly(amic acid) solution. This solution was diluted with DMAc (3 mL), poured into a glass dish, followed by vacuum evaporation of DMAc at 50° C., and heat-treated at: 100° C./1 h, 150° C./1 h, 175° C./1 h, 200° C./2 h, 250° C./1 h and 300° C./1 h to form imidized polymers. The film thickness was approximately 20-100 μm. T$_g$=352° C. (DMA). FT-IR (KBr, cm$^{-1}$): 3067 (Ar—H), 1785, 1721 (imide), 1624, 1582, 1486, 1359, 1231, 1205, 1189, 1137, 1080, 1008, 982, 961, 835, 719, 705, 649, 546.

Example 21: Procedure for the preparation of azoODA-OPDA polyimide

The OPDA polyimide was prepared from 4,4'-oxybis[4-(4-aminophenyldiazenyl)phenyl] (4a; Azo-ODA, 4, 0.7463 g, 1.836 mmol), OPDA (11e; 0.5668 g, 1.836 mmol) and DMAc (8 mL) using the same procedure as described above to form the corresponding imidized polymer in the form of thin films. The film thickness was approximately 20-100 μm. $T_g$=273° C. (DMA). FT-IR (KBr, cm$^{-1}$): 3066 (Ar—H), 1777, 1712 (imide), 1579, 1486, 1475, 1436, 1353, 1228, 1138, 1110, 1073, 1009, 958, 934, 835, 741, 546.

Example 22: Procedure for the preparation of azoODA-PMDA polyimide

The azoODA-PMDA polyimide (13a) was prepared from 4,4'-oxybis[4-(4-aminophenyldiazenyl)phenyl] (Azo-ODA, 4a; 0.8000 g, 1.950 mmol), PMDA (11c; 0.4272 g, 1.950 mmol) and DMAc (8 mL) using the same procedures described above to form imidized polymers. The film thickness was approximately 20-100 μm. $T_g$>400° C. (DMA). FT-IR (KBr, cm$^{-1}$): 3047 (Ar—H), 1776, 1715 (imide), 1579, 1485, 1349, 1230, 1182, 1137, 1112, 1081, 1008, 950, 916, 820, 719, 624, 546.

Example 23: Procedure for the preparation of azo6FBPA-6FDA polyimide

The azo6FBPA-6FDA polyimide was prepared from 2,2-bis{4-[4-(4-aminophenyldiazenyl)phenoxy]phenyl}hexafluoropropane (Azo-6FBPA, 10d; 0.8000 g, 1.100 mmol), 6FDA (0.4891 g, 1.100 mmol) and DMAc (8 mL) using the same procedure as described above to form the corresponding imidized polymer in the form of thin films. The film thickness was approximately 20-100 μm. $T_g$=307° C. (DMA) FT-IR (KBr, cm$^{-1}$): 3052 (Ar—H), 1785, 1723 (imide), 1591, 1490, 1362, 1238, 1202, 1170, 1137, 1109, 1015, 983, 953, 832, 720, 704, 646, 546.

Example 24: Synthesis of 1,2-bis(4-aminophenoxy)benzene (pop-APB)

(i) 1,2-Bis(4-nitrophenoxy)benzene: Into a 500 mL three-necked flask equipped with a magnetic stir bar and nitrogen inlet and outlet were placed catechol (15.0 g, 0.135 mol), 4-fluoronitrobenzene (40.2 g, 0.285 mol), anhydrous $K_2CO_3$ (42.9 g, 0.310 mol) and dry DMF (130 mL). The mixture was stirred at room temperature for 24 h. It was poured into a mixture of methanol/water (1:2). After the precipitate was collected by filtration, washed with water and dried, a yellow solid was obtained in a yield of 25.5 g (82.3%). The crude product was recrystallized from acetic acid (200 mL) to afford 22.5 (72.5%) of yellow crystals: m.p. 133.8-135.7° C. (lit. $^1$136-138° C.). $^1$H-NMR (d$_6$-DMSO, δ in ppm): 6.99-7.02 (d, 4H, Ar—H), 7.436-7.440 (d, 4H, Ar—H), 8.15-8.18 (d, 4H, Ar—H). $^{13}$C-NMR (d$_6$-DMSO, δ in ppm): 116.69, 123.46, 126.07, 127.58, 142.47, 145.37, 162.03.

(ii) 1,2-Bis(4-aminophenoxy)benzene (pop-APB): Into a 500 mL three-necked flask equipped with a magnetic stir bar and nitrogen inlet and outlet were placed 1,2-bis(4-nitrophenoxy)benzene (10.5 g, 0.030 mol), 5% Pd/C (0.2 g) and ethanol (150 mL). The mixture was stirred at 85° C. and hydrazine monohydrate (30 mL) was added drop-wise within 1 h. After the addition had been completed, the mixture was heated at 85° C. for another 4 h. Then decolorizing carbon (0.5 g) was carefully added and then filtered rapidly after 5 min of stirring. The filtrate was allowed to cool and stored in a refrigerator overnight to afford 7.1 g (81.0%) of colorless needles: m.p. 137-138° C. (lit. 137-138° C.). The filtrate was concentrated under reduced pressure and a suitable amount of water was added to give 1.0 g (11.4%) of white crystals: m.p. 137-138° C. Thus, the total yield was 47 g (82.4%). $^1$H-NMR (d$_6$-DMSO, δ in ppm): 4.88 (s, 4H, NH$_2$), 6.53-6.56 (d, 4H, Ar—H), 6.68-6.71 (d, 4H, Ar—H), 6.75-6.84 (d, 2H, Ar—H), 6.94-6.98 (d, 2H, Ar—H). $^{13}$C-NMR (d$_6$-DMSO, δ in ppm): 114.84, 118.88, 119.38, 123.14, 144.79, 146.71, 148.42.

Example 25: Representative "sequential addition" procedure for preparation of linear blocky azobenzene-containing 6FDI polyimides (L-ppp-6FDI)

1,4-Bis(4-aminophenoxy)benzene (APB, 15d; 0.4093 g, 1.40 mmol) and DMAc (8.0 mL) were added to a 50-mL 3-necked flask equipped with a magnetic stirrer, nitrogen inlet and outlet, and stirred under dry nitrogen at room temperature for 30 min. 6FDA (0.8885 g, 2.00 mmol) was then introduced to the resulting solution. The light yellow solution was agitated at room temperature for 24 h to afford a poly(amic acid) solution. 2,2-Bis{4-[4-(4-aminophenyldiazenyl)phenoxy]phenyl}propane (10a, 0.3712 g, 0.600 mmol) was added and the mixture was agitated for 2 h. Then, the mixture poured into a glass petri dish, followed by vacuum evaporation of DMAc at 50° C., and heat-treated according to following schedule: 100° C./2 h, 150° C./2 h, 175° C./1 h, 200° C./2 h, 250° C./1 h and 300° C./1 h to form polyimide films. The film thickness was approximately 20-100 μm. ATR-IR (film): 1784, 1719, 1590, 1504, 1488, 1365, 1205, 1138, 1081, 982, 961, 828, 719 cm$^{-1}$. This procedure was followed to prepare other linear (L) 6FDI-based copolyimides, designated as L-xxx-6FDI, where xxx (=ppp, pmp, pop and mmm) corresponds to the particular diamine as indicated in FIG. 10 inset.

Example 26: Representative "single mixing" procedure for azoBPA-6FDI-30 to illustrate the synthesis of azobenzene-containing random copolyimides 2,2-Bis{4-[4-(4-aminophenyldiazenyl)phenoxy]phenyl}propane (7a; 0.3712 g, 0.600 mmol), APB (10, 0.4093 g, 1.400 mmol) and DMAc (8 mL) were added to a 25 mL 3-necked flask equipped with a magnetic stirrer, nitrogen inlet and outlet, and stirred under dry nitrogen at room temperature for 30 min. 6FDA (0.8888 g, 2.000 mmol) were then charged. The light yellow solution was agitated at room temperature for 24 h to afford a viscous poly(amic acid) solution, which was poured into a glass dish, followed by vacuum evaporation of DMAc at 50° C., and heat-treated at: 100° C./2 h, 150° C./2 h, 175° C./1 h, 200° C./2 h, 250° C./1 h and 300° C./1 h to form imidized polymers. The film thickness was approximately 20-100 μm. FT-IR (KBr, cm$^{-1}$): 3070 (Ar—H), 2967 (CH$_3$), 1784, 1721 (imide), 1586, 1488, 1479, 1449, 1364, 1237, 1190, 1139, 1099, 964, 834, 779, 718, 550.

Three more copolyimides (12b-d, labeled as azoBPA-6FDI-xx, where xx stands for the azoBPA content in mol %) were prepared similarly.

Example 27: Physical Characterization and Photomechanical Properties of Polyimides Wide Angle X-ray Diffraction (WAXD): The morphology of the materials was characterized with wide-angle X-ray diffraction (WAXD). All the azo-polyimides except azo-ODA-OPDA are amorphous, evident in the featureless diffraction patterns of these materials (see FIG. 4). It is interesting that OPDA azo-polyimide not PMDA one (most rigid dianhydride) showed crystallinity. Flexible ether linkage in both diamine and dianhydride probably attributes to the crystalline structures of azo-ODA-OPDA.

Density Determination: The density of each polymer film is determined based on Davy's principle of hydrostatic suspension using a mixture of carbon tetrachloride and ethanol as the suspension medium. Small pieces of azopolyimide film are suspended individually in a mixture of carbon tetrachloride and methanol in a 10 mL graduated cylinder, which had previously been tared. The total solvent volume is between 9.4 and 10 mL, and the films re-suspended around the 5 mL mark when the solvent is weighed. The mass of the solution and the total volume are used to calculate a density. The films did not swell in the solvent mixture. The resulting density values for the azopolyimide films are summarized in Table 1 below.

TABLE 1

Physical Characterization of Linear azo-Polyimide

| Sample | Density (g/cc) | $E^a$ (GPa) | $T_g{}^a$ (° C.) | $T_{d5\%}{}^b$ (° C.) in air | $T_{d5\%}{}^b$ (° C.) in nitrogen |
|---|---|---|---|---|---|
| azoBPA-PMDA | 1.363 | 2.51 ± 0.16 | 307 | 451 | 424 |
| azoBPA-BPDA | 1.355 | 1.99 ± 0.42 | 302 | 458 | 427 |
| azoBPA-BTDA | 1.347 | 1.66 ± 0.14 | 294 | 456 | 422 |
| azoBPA-6FDA | 1.339 | 1.37 ± 0.17 | 284 | 474 | 421 |
| azoBPA-OPDA | 1.304 | 1.34 ± 0.10 | 276 | 451 | 420 |

Notes:
$^a T_g$ measured from the peak of tan delta (DMA) as an average value taken from 4 measurements;
$^b$Temperature at which 5% weight loss as recorded on TGA thermogram with a heating rate of 10° C./min.

Figures 5A, 5B:
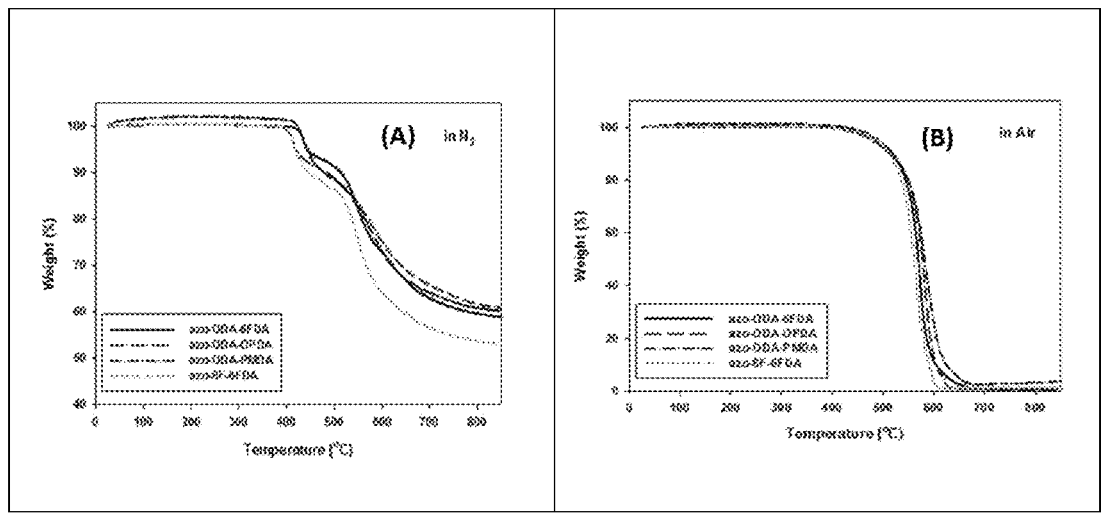
FIGS. 5A-5B shows two thermogravimetric analysis graphs of various azo-polyimides under nitrogen (5A, left) and air (5B, right) atmospheres.
Figures 6A, 6B, 6C, 6D, 6E, 6F, 6G, 6H, 6I, 6J:
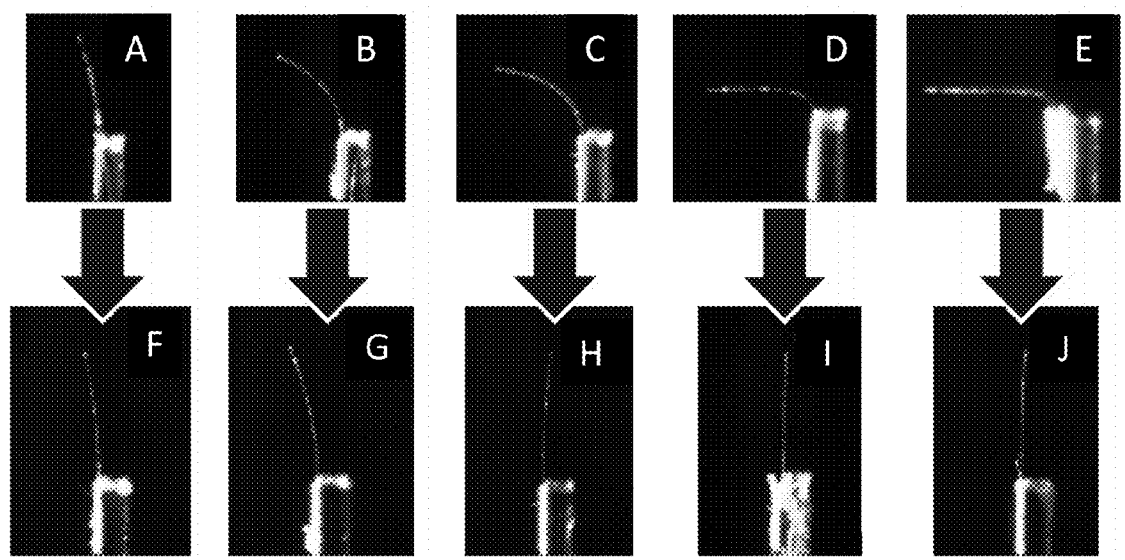
FIGS. 6A-6E are photographs showing photoinduced bending of various polyimides (A) azoBPA-PMDA; (B) azoBPA-BPDA; (C) azoBPA-BTDA; (D) azoBPA-6FDA; and (E) azoBPA-OPDA, upon exposure to linearly polarized 445 nm light (E//x) at 120 mW/cm² for 1 hour.
FIGS. 6F-6J are photographs showing relaxation of various polyimides (A) azoBPA-PMDA; (B) azoBPA-BPDA; (C) azoBPA-BTDA; (D) azoBPA-6FDA; and (E) azoBPA-OPDA, under dark for 10 days, after the exposure to linearly polarized 445 nm light (E//x) at 120 mW/cm² for 1 hour shown in FIGS. 6A-6E.

Thermogravimetric Analysis (TGA):

Thermal stability of the polyimides and copolyimides was studied by TGA. As shown in FIGS. 5A-5B, the films were heated in both nitrogen (5A) and air (5B) with a heating rate of 10° C./min. The polymers show excellent short-term thermal/thermo-oxidative stability. No thermal or thermo-oxidative degradation was observed up to 450° C. in air and 420° C. in nitrogen atmosphere.

Dynamic Mechanical Analysis (DMA):

DMA of the polyimide and copolyimide films is conducted in a nitrogen atmosphere with a heating rate of 4° C./min on a TA Instruments® DMA Q800 to obtain the glass transition temperature and the storage modulus. The glass transition temperature ($T_g$) is measured from the peak value of the tan δ curve. The DMA results are summarized in the Table 2 below.

Photomechanical Characterization

Photomechanical deformations were characterized with irradiation of linearly polarized 445 nm light. All measurements were conducted with light polarization parallel to long axis of the cantilevers (E//x) while the cantilever dimension was kept as 6 mm (L)×0.1 mm (W)×0.02 mm (T). As shown in FIGS. 6A-6J, photoinduced bending (6A-6E) and relaxation (6F-6J) of the polyimide cantilevers were monitored with linearly polarized 445 nm light exposure (E//x) at 120 mW/cm² for 1 h and dark relaxation for 10 days, respectively. Polyimide films composed with rigid PMDA and BPDA (tensile modulus≥2 GPa) had smaller magnitude of bending than other polyimides and partial photofixing was found upon removal of the irradiation for 10 days. In contrast, softer polyimides demonstrated large photoinduced deflection and complete relaxation under dark.

Figure 7A:
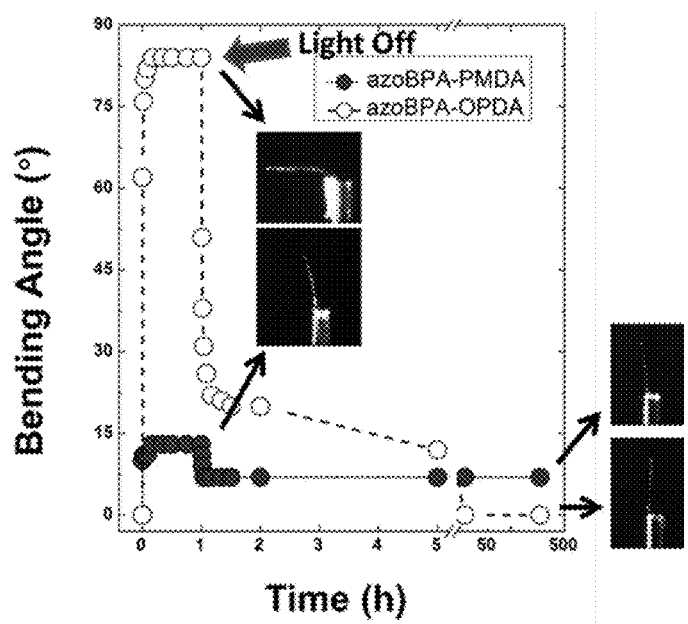
FIGS. 7A-7B are graphs showing time-resolved measurements of photoinduced bending (A) and photogenerated stress (B) of azoBPA-PMDA and azoBPA-OPDA.
Figure 7B:
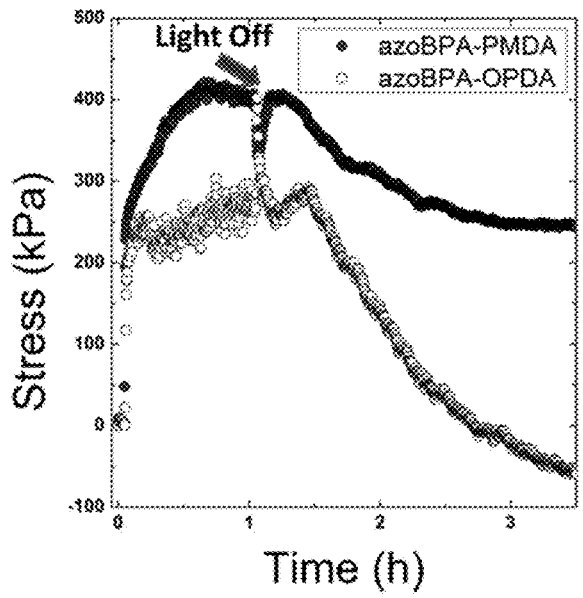

The photoinduced bending (FIG. 7A) and unbending (relaxation) (FIG. 7B) were further investigated with the most rigid and soft azoBPA-PMDA and azoBPA-OPDA. As shown in FIG. 7A, time-resolved measurement of photomechanical bending was conducted to compare the response time scale of photogenerated strain and relaxation. Both polyimides reached the equilibrium in 30 min for photoinduced bending. In the case of relaxation, azoBPA-OPDA required 2 days of dark relaxation for full recovery of initial unbent state while only was necessary few minutes for photofixation of azoBPA-PMDA into a bent state with slight relaxation.

In addition to bending which is dependent to geometry, geometry independent photogenerated stress of azoBPA-PMDA and azoBPA-OPDA were measured by DMA with irradiation of linearly polarized (E//x) blue light. Reorientation of polymer chains perpendicular to long axis of the cantilever caused contractile stress, which is measured as positive stress by DMA in tension. Again, photogenerated stress reached the equilibrium in 30 min for both polyimides. The greater magnitude of photogenerated stress was measured from azoBPA-PMDA although larger deformation was found from azoBPA-OPDA. This phenomenon is again related to bending modulus in Euler-Bernoulli beam theory and stiffer polymer films require greater stress to be deformed. Under dark relaxation, ca. 250 kPa of stress remained for azoBPA-PMDA and full recovery of initial force and even negative force was measured for azoBPA-OPDA.

Example 28: Physical Characterization and Photomechanical Properties of Co-Polyimides: Linear Blocky azo-Polyimides (L-xxx-6FDI Series)

Dynamic Mechanical Analysis (DMA) of the polyimide and copolyimide films is conducted in a nitrogen atmosphere

TABLE 2

Tensile properties of polyimide films

| Sample | Tensile Modulus (GPa) | Yield Stress (MPa) | Ultimate Tensile Strength (MPa) | Strain to Failure (%) | Toughness (MJ/m³) |
|---|---|---|---|---|---|
| azoBPA-PMDA | 2.51 ± 0.16 | 99.1 ± 8.3 | 147.0 ± 11.0 | 147.5 ± 17.9 | 213.7 ± 57.7 |
| azoBPA-BPDA | 1.99 ± 0.42 | 86.5 ± 6.6 | 95.5 ± 5.6 | 127.5 ± 18.2 | 121.5 ± 10.6 |
| azoBPA-BTDA | 1.66 ± 0.14 | 92.6 ± 12.3 | 94.1 ± 10.3 | 82.4 ± 20.9 | 63.5 ± 12.1 |
| azoBPA-6FDA | 1.37 ± 0.17 | 75.0 ± 4.7 | 75.1 ± 4.7 | 23.3 ± 4.1 | 19.0 ± 4.1 |
| azoBPA-OPDA | 1.34 ± 0.10 | 63.7 ± 3.0 | 81.7 ± 1.2 | 257.6 ± 5.8 | 228.4 ± 3.5 | with a heating rate of 4° C./min on a TA Instruments® DMA Q800 to obtain the glass transition temperature and the storage modulus. The glass transition temperature ($T_g$) is measured from the peak value of the tan δ curve. The DMA results are summarized in the Table 3 below.

TABLE 3

Physical Characterization of Linear Blocky azo-Polyimides

| Sample | $T_g{}^a$ (° C.) | $E^b$ (GPa) | $T_{d5\%}{}^c$ (° C.) in air | $T_{d5\%}{}^c$ (° C.) in nitrogen |
|---|---|---|---|---|
| L-ppp-6FDI | 303 | 2.38 | 493 | 468 |
| L-pmp-6FDI | 277 | 2.64 | 496 | 472 |
| L-pop-6FDI | 277 | 2.05 | 486 | 472 |
| L-mmm-6FDI | 248 | 2.27 | 488 | 451 |

Thermogravimetric Analysis (TGA)

Thermal stability of the copolyimides was studied by TGA. The films were heated in both nitrogen and air with a heating rate of 10° C./min. The polymers show excellent short-term thermal/thermo-oxidative stability. No thermal or thermo-oxidative degradation is observed up to 450° C. in air and 420° C. in nitrogen atmosphere (results not shown).

that of the neat CP2 (6FDA-APB) polyimide film. The $T_g$ values (237° C.-269° C.) of the azobenzene-containing copolyimides increase with the concentration of azoBPA diamine. Flory-Fox equation has been used to calculate the $T_g$'s (values in parentheses in Table 4 below) of copolyimides, which show a good agreement with the measured values by DMA. The tensile moduli (E) of the azoBPA-6FDA-xx films initially decrease with the concentration of azoBPA, which prove that azoBPA is less rigid than APB.

Thermal Properties. Thermal stability was evaluated by TGA. All the polymers display high thermal stability with 5 wt % weight loss temperatures occurring between 474° C. to 498° C. in air and 420° C. to 456° C. in nitrogen. Interesting, all the polymers have 26° C. to 54° C. higher degradation temperatures in air than in nitrogen. Generally speaking, non-bis(azobenzene)-containing polyimide polymers like CP2 should have higher degradation temperatures in nitrogen than in air (Table 4 below). The unusual results can be explained by azo double bonds being oxidized by oxygen and gain weight in air.

TABLE 4

Composition and properties of copolyimide films

| Sample | Dianhydride (mol %) | azoBPA (mol %) | APB (mol %) | $T_g{}^a$ (° C.) | $E^b$ (GPa) | $T_{d5\%}{}^c$ (° C.) air | $T_{d5\%}{}^c$ (° C.) $N_2$ |
|---|---|---|---|---|---|---|---|
| CP2$^d$ | 100 | 0 | 100 | 219 | 1.90 ± 0.15 | 526 | 530 |
| azoBPA-6FDA-30 | 100 | 30 | 70 | 237 (240$^e$) | 1.74 ± 0.21 | 498 | 456 |
| azoBPA-6FDA-35 | 100 | 35 | 65 | 243 (244$^e$) | 1.57 ± 0.12 | 493 | 442 |
| azoBPA-6FDA-45 | 100 | 45 | 55 | 248 (250$^e$) | 1.48 ± 0.10 | 484 | 439 |
| azoBPA-6FDA-70 | 100 | 70 | 30 | 269 (266$^e$) | 1.35 ± 0.09 | 477 | 424 |
| azoBPA-6FDA | 100 | 100 | 0 | 284 | 1.10 ± 0.26 | 474 | 420 |

Notes:
$^a T_g$ measured from the peak of tan delta (DMA) as an average value taken from 4 measurements;
$^b$modulus determined in tension at 25° C. as average from 5 specimens per sample;
$^c$Temperature at which 5% weight loss recorded on TGA thermogram obtained with a heating rate of 10° C./min;
$^d$a non-bis(azobenzene)-containing polyimide from 6FDA and APB;
$^e$calculated from Flory-Fox equation $1/T_g = w_1/T_{g,1} + w_2/T_{g,2}$, where $w_1$ and $w_2$ are weight fractions of components 1 and 2, respectively.

Example 28: Physical Characterization and Photomechanical Properties of Co-Polyimides: Linear Random azo-copolyimides (azoBPA-6FDA-xx Series; FIG. 10)

The concentration of azobenzene moieties was varied in the azo-copolyimide (azoBPA-6FDA-xx; FIG. 10) films by using specific amounts (i.e. 30, 35, 45, and 70 mol %) of azoBPA monomer (10a) in the respective PAA/DMAc solutions. The molar ratios of the ternary mixtures (6FDA:APB:azoBPA) are listed in Table 4. The glass transition temperature ($T_g$) of the neat Azo-6FDA-PI copolyimide is 284° C. by dynamic mechanical analysis (DMA), much higher than

Example 29: Photomechanical Characterization of Linear Block azo-coPolyimides L-xxx-6FDI (FIGS. 11A-11B)

For all photomechanical benchmarking experiments, azo-copolyimide films in the form of cantilevers are held at approximately the same distance from a source of light. The employed light source is blue-green irradiation, which allows all-optical control of forward and reverse bending (or contractile and expansive stress) by adjusting the orientation of the linear polarization of the irradiating light. Blue-green irradiation is also known to induce trans-cis-trans reorientation of azobenzene chromophores. In FIG. 11A, bending angles (at 1 hour light exposure) and with 3 days dark relaxation were plotted for linear block azo-coPolyimides series. In FIG. 11B, time resolved bending angle for various linear azo-copolyimides series is plotted. All measurement employed films of dimension 6 mm (L)×0.1 mm (W)×20 μm (T) and the films were subjected to 445 nm light (E//x) at 120 mW/cm² intensity.

The connectivity of the phenylene rings strongly influences the resulting response as presented graphically in FIGS. 11A-11B. Upon the irradiation with linearly polarized (E//x) 445 nm light (see FIG. 11A), the largest magnitude photomechanical cantilever deflection was observed from L-ppp-6FDI while the smallest magnitude deflection was found from L-mmm-6FDI. After the relaxation in dark over the course of 3 days, L-ppp-6FDI had more shape retention behavior and L-mmm-6FDI fully recovered the initial flat geometry. The photomechanical deformation and shape retention behaviors of both L-pmp-6FDI and L-pop-6FDI were in between L-ppp-6FDI and L-mmm-6FDI. Time-resolved photomechanical response was monitored and recorded, as shown in FIG. 11B. In contrast to the magnitude of bending and shape retention, L-ppp-6FDI responded most slowly and the fastest response was found from L-mmm-6FDI.

Example 30: Photomechanical Characterization of Linear Random azo-coPolyimides (azoBPA-6FDA-xx; see FIG. 12)

(i) Photo-Induced Bending:

The azobenzene chromophores in the polyimide materials examined here absorb 445 nm light, and a small portion of these chromophores reorient in the direction perpendicular to light polarization through trans-cis-trans reorientation mechanism. As shown in FIG. 12, time-resolved measurements are shown of photomechanical responses of random 6FDA-coPIs upon exposure to linearly polarized (E//x) 445 nm light at 120 mW/cm² for 1 h. Images were taken at 60 min time mark and labeled A1-E1 denoting different 6FDA molar ratio (i) 0, (ii) 0.35, (iii) 0.45, (iv) 0.70, and (v) 1.00. Images labeled A2-E2 were taken after 10 days relaxation at dark. All measurements were conducted with cantilever geometry of 6 mm (L)×0.1 mm (W)×20 μm (T).

While the cantilever of CP2 (i.e. 6FDA-APM polyimide having no azobenzene units) was not responsive to the light, and the bending angles of azoBPA copolyimides increased with radiation duration. The copolyimides with low concentration of azobenzene units quickly reached maximum bending angles in 10-20 min. The copolyimides with high concentration of azobenzene units needed more time to reach equilibrium (~1 h). After all the samples are exposed to the 445 nm light at 120 mW/cm² for 1 h, they were stored in the dark to relax for 10 days. The copolyimides with high concentration of azobenzene fully recovered to the original position, showing photoelastic properties. The copolyimides with low concentration of azobenzene units still kept certain bending positon, showing photofixing properties.

As shown in FIG. 13, photoinduced piezoelectricity of azoBPA-6FDA with (A) draw ratio of 1 and (B) draw ratio of 3. Negligible piezoelectricity was found without hot-drawing, while considerable piezoelectricity was measured from draw ratio 3 sample. In FIG. 13, filled rectangle, unfilled triangle, and filled circle indicate noise signal, 1.2 Hz, and 5 Hz light on-off frequency, respectively. Linearly polarized (E//x) 445 nm light was employed at 270 mW/cm².

While the present invention has been illustrated by the description of one or more embodiments thereof, and while the embodiments have been described in considerable detail, they are not intended to restrict or in any way limit the scope of the appended claim to such detail. Additional advantages and modification will be readily apparent to those skilled in the art. The invention in its broader aspects is therefore not limited to the specific details, representative apparatus and methods and illustrative examples shown and described. Accordingly, departures may be made from such details without departing from the scope or the spirit of the general inventive concept exemplified herein.

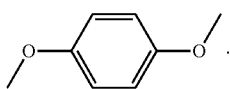

8. The bis(azobenzene)-containing polyimide of claim 3, wherein L is
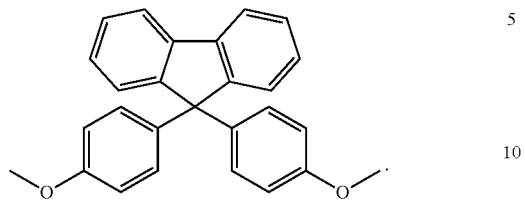

What is claimed is:

1. A polymer comprising a bis(azobenzene)-diamino monomer defined by a general chemical formula (I):

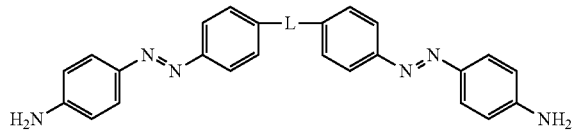

wherein L' is selected from the group consisting of

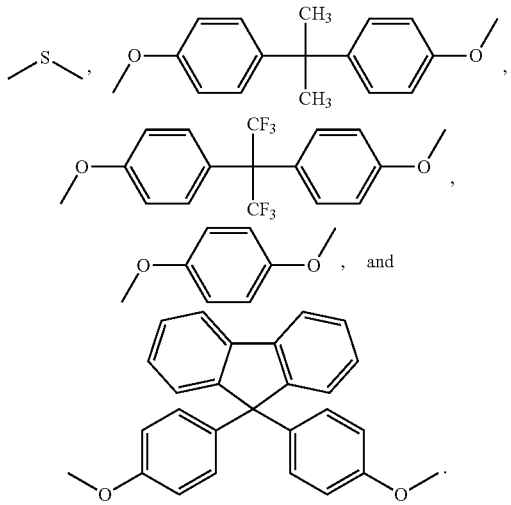

2. A bis(azobenzene)-containing polyamic acid, comprising a reaction product of a bis(azobenzene)-diamino monomer and a dianhydride, the bis(azobenzene)-diamino monomer defined by a general chemical formula (I):

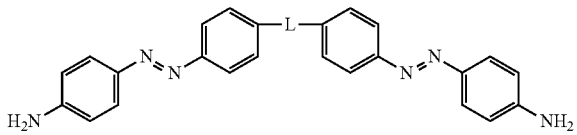

wherein L' is selected from the group consisting of

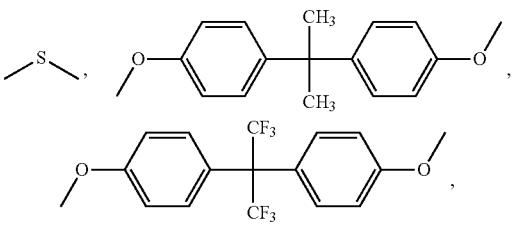

-continued

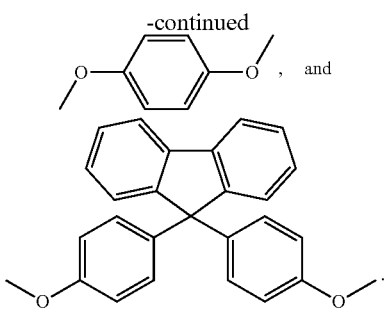
and

3. A bis(azobenzene)-containing polyimide defined by a general chemical formula (II):

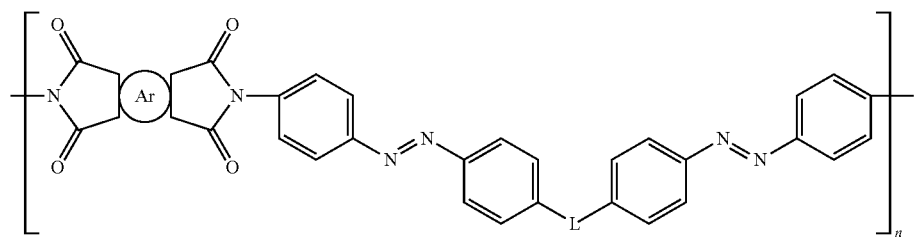

wherein n is a degree of polymerization;
wherein

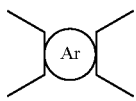

is selected from the group consisting of

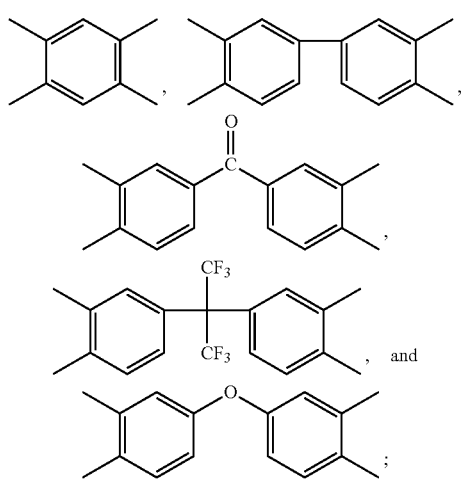

and
wherein -L- is selected from the group consisting of

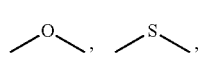

-continued

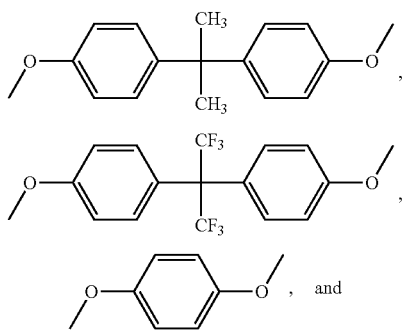
and

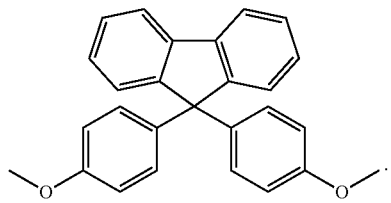

4. The bis(azobenzene)-containing polyimide of claim 3, wherein L is —O—.

5. The bis(azobenzene)-containing polyimide of claim 3, wherein L is —S—.

6. The bis(azobenzene)-containing polyimide of claim 3, wherein L is

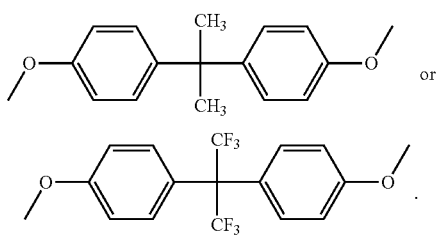 or

7. The bis(azobenzene)-containing polyimide of claim 3, wherein L is